(12) United States Patent
Toriyama et al.

(10) Patent No.: US 12,306,171 B2
(45) Date of Patent: May 20, 2025

(54) METHOD FOR DETECTING INDICATOR OF IMMUNE-RELATED DISEASE

(71) Applicants: MANDOM CORPORATION, Osaka (JP); OSAKA UNIVERSITY, Suita (JP); NATIONAL INSTITUTES OF BIOMEDICAL INNOVATION, HEALTH AND NUTRITION, Ibaraki (JP)

(72) Inventors: Manami Toriyama, Suita (JP); Fumitaka Fujita, Osaka (JP); Fumihiro Okada, Osaka (JP); Ken Ishii, Ibaraki (JP)

(73) Assignees: MANDOM CORPORATION, Osaka (JP); OSAKA UNIVERSITY, Suita (JP); NATIONAL INSTITUTES OF BIOMEDICAL INNOVATION, HEALTH AND NUTRITION, Ibaraki (JP)

( * ) Notice: Subject to any disclaimer, the term of this patent is extended or adjusted under 35 U.S.C. 154(b) by 1074 days.

(21) Appl. No.: 16/977,918

(22) PCT Filed: Mar. 8, 2019

(86) PCT No.: PCT/JP2019/009313
§ 371 (c)(1),
(2) Date: Sep. 3, 2020

(87) PCT Pub. No.: WO2019/172419
PCT Pub. Date: Sep. 12, 2019

(65) Prior Publication Data
US 2021/0003546 A1   Jan. 7, 2021

(30) Foreign Application Priority Data
Mar. 9, 2018   (JP) .................. 2018-042851

(51) Int. Cl.
*G01N 33/483* (2006.01)
*G01N 33/569* (2006.01)

(52) U.S. Cl.
CPC .... *G01N 33/4833* (2013.01); *G01N 33/56966* (2013.01); *G01N 2800/24* (2013.01); *G01N 2800/52* (2013.01)

(58) Field of Classification Search
CPC ......... G01N 33/4833; G01N 33/56966; G01N 2800/24; G01N 2800/52; G01N 33/5076;
(Continued)

(56) References Cited

U.S. PATENT DOCUMENTS

| 6,537,977 B1 | 3/2003 | Kyogashima et al. |
| 2004/0115237 A1 | 6/2004 | Kelso et al. |

(Continued)

FOREIGN PATENT DOCUMENTS

| CN | 1627074 A | 6/2005 |
| JP | 2004-533904 A | 11/2004 |

(Continued)

OTHER PUBLICATIONS

Hassounah et al. Primary cilia are lost in preinvasive and invasive prostate cancer. PLoS One. Jul. 2, 2013;8(7):e68521. (Year: 2013).*

(Continued)

*Primary Examiner* — Rebecca M Giere
*Assistant Examiner* — Alexander Alexandrovic Volkov
(74) *Attorney, Agent, or Firm* — XSENSUS LLP

(57) ABSTRACT

Provided is a method whereby an objective indicator of an immune-related disease can be rapidly and easily detected, the method comprising detecting, as an indicator of an immune-related disease, a difference in the result of observing a primary cilium of an immune-related cell between a subject specimen and a normal specimen.

9 Claims, 13 Drawing Sheets

(58) Field of Classification Search
CPC ... G01N 33/5697; A61K 31/573; A61P 37/06; A61P 43/00
See application file for complete search history.

(56) References Cited

U.S. PATENT DOCUMENTS

| | | |
|---|---|---|
| 2007/0172448 A1 | 7/2007 | Hu |
| 2007/0179091 A1 | 8/2007 | de Sauvage et al. |
| 2012/0164100 A1 | 6/2012 | Li et al. |
| 2015/0164940 A1 | 6/2015 | Tanaka et al. |
| 2016/0333073 A1 | 11/2016 | Shima et al. |

FOREIGN PATENT DOCUMENTS

| | | |
|---|---|---|
| JP | 2009-526752 A | 7/2009 |
| JP | 2017-506220 A | 3/2017 |
| WO | 97/11096 A1 | 3/1997 |
| WO | 2014/050912 A1 | 4/2014 |
| WO | 2015/110809 A2 | 7/2015 |

OTHER PUBLICATIONS

Lau et al. The kinesin motor protein Kif7 is required for T-cell development and normal MHC expression on thymic epithelial cells (TEC) in the thymus. Oncotarget. Apr. 11, 2017;8(15):24163-24176. (Year: 2017).*
Hua et al. Primary cilia proteins: ciliary and extraciliary sites and functions. Cell Mol Life Sci. May 2018;75(9):1521-1540. doi: 10.1007/s00018-017-2740-5. Epub Jan. 5, 2018. (Year: 2018).*
Jul. 2024 Subject Matter Eligibility Examples 47-49 (Year: 2024).*
Prosser et al., "Centrin 2 regulates CP110 removal in primary cilium formation", The Journal of Cell Biology, vol. 208, No. 6, pp. 693-701, published on Mar. 9, 2015, cited in the specification.
Sugier et al., "A novel role for ciliary function in atopy: ADGRV1 and DNAH5 interactions", J Allergy Clin Immunol, Sep. 18, 2017, 141 (5), pp. 1659-1667. ell, cited in ISR.
Oud et al., "Cellular ciliary phenotyping indicates pathogenicity of novel variants in IFT140 and confirms a Mainzer-Saldino syndrome diagnosis", CILIA, Feb. 23, 2018, 7:1, cited in ISR (9 pages).
Khan et al., "Identification of drugs that restore primary cilium expression in cancer cells", Oncotarget, Mar. 1, 2016, 7 (9), pp. 9975-9992, cited in ISR.
Dalbay et al., "Adipogenic Differentiation of hMSCs is Mediated by Recruitment of IGF-1R Onto the Primary Cilium Associated With Cilia Elongation", Stem Cells, Jun. 2015, 33 (6), pp. 1952-1961, cited in ISR.
Workman et al., "Effects of ophthalmologic solutions on sinonasal ciliated epithelium", Int Forum Allergy Rhinol., Aug. 2017, 7 (8), pp. 801-808, cited in ISR.

International Search Report dated Jun. 11, 2019, issued in counterpart International Application No. PCT/JP2019/009313 (4 pages).
Office Action issued on Feb. 24, 2023, in corresponding Chinese patent Application No. 201980007173.7, 7 pages.
Office Action dated Aug. 31, 2021, issued in counterpart Japanese patent application No. 2020-505131 (w/ English translation; 7 pages).
Office Action dated Jul. 23, 2021, issued in Korean patent application No. 10•2020-7019220 (10 pages).
Wann, A. K. T. et al., Primary cilia elongation in response to interleukin-1 mediates the inflammatory response, Cell. Mol. Life Sci. (2012) vol. 69, pp. 2967-2977.
Smith, C. M. et al., "Ciliary dyskinesia is an early feature of respiratory syncytial virus infection", European Respiratory Journal, 2014, vol. 43, No. 2, pp. 485-496, cited in EP Extended European Search Report dated Mar. 29, 2022. (12 pages).
Khan N. A. et al., "Identification of drugs that restore primary cilium expression in cancer cells", Oncotarget, 2016, vol. 7, No. 9, pp. 9975-9992, cited in EP Extended European Search Report dated Mar. 29, 2022. (18 pages).
Strugnell, G. E. et al., "Primary cilium expression in cells from normal and aberrant human skin", Journal of Submicroscopic Cytology and Pathology, 1996, vol. 28, No. 2, pp. 215-225, cited in EP Extended European Search Report dated Mar. 29, 2022. (11 pages).
Elofsson, R. et al., "The ciliated human keratinocyte", Journal of Ultrastructure Research, 1984, vol. 37, No. 3, pp. 212-220, cited in EP Extended European Search Report dated Mar. 29, 2022. (9 pages).
Thomas, B. et al., "Ciliary dysfunction and ultrastructural abnormalities are features of severe asthma", Journal of Allergy and Clinical Immunology, 2010, vol. 126, No. 4, pp. 722-729, cited in EP Extended European Search Report dated Mar. 29, 2022. (10 pages).
Ezratty, E. J. et al., "A Role for the Primary Cilium in Notch Signaling and Epidermal Differentiation during Skin Development", Cell, 2011, vol. 145, No. 7, pp. 1129-1141, cited in EP Extended European Search Report dated Mar. 29, 2022. (13 pages).
Forcioli-Conti, N. et al., "The primary cilium undergoes dynamic size modifications during adipocyte differentiation of human adipose stem cells", Biochemical and Biophysical Research Communications, 2015, vol. 458, No. 1, pp. 117-122, cited in EP Extended European Search Report dated Mar. 29, 2022. (6 pages).
Chen, H. et al., "Glucocorticoid dexamethasone regulates the differentiation of mouse conducting airway epithelial progenitor cells", Steroids, 2014, vol. 80, pp. 44-50, cited in EP Extended European Search Report dated Mar. 29, 2022. (7 pages).
Extended (Supplementary) European Search Report dated Mar. 29, 2022, issued in counterpart EP application No. 19764929.6. (19 pages).

\* cited by examiner

5μm

100μm

METHOD FOR DETECTING INDICATOR OF IMMUNE-RELATED DISEASE

TECHNICAL FIELD

The present invention relates to a method for detecting an index of an immune-related disease. More specifically, the present invention relates to a method for detecting an index of an immune-related disease and a method for assisting diagnosis of the immune-related disease, by utilizing a primary cilium of an immune-related cell, which are useful for examination of the immune-related disease, assistance in diagnosis of the immune-related disease, development of a therapeutic agent for the immune-related disease, development of a quasi-drug or a cosmetic component for suppressing the immune-related disease, and the like; an examination kit for an immune-related disease used for these methods; a method for evaluating a suppression effect on an immune-related disease and a method for evaluating a test sample, by utilizing the primary cilium of the immune-related cell; an immune function-controlling agent; and an agent for removing a primary cilium of an immune-related cell.

BACKGROUND ART

A primary cilium is a nonmotile cellular organ which is mainly present on the surface of a non-immune cell such as a human retinal pigment epithelial cell. It has been known that an abnormality of a primary cilium of a human retinal pigment epithelial cell causes retinal degeneration.

On the other hand, it has been reported that primary cilium formation is induced in an immune cell, when an established T cell line and an established B cell line are maintained in a serum starvation state (see, for example, Non-patent Literature 1). At present, however, the present inventors have not found a document concretely disclosing the relationship between a primary immune cell and a primary cilium function.

PRIOR ART LITERATURE

Non-Patent Literature

Non-patent Literature 1; Suzanna L. Prosser et al., "Centrin 2 regulates CP110 removal in primary cilium formation", The Journal of Cell Biology, Vol. 208, No. 6, pp. 693-701, published on Mar. 9, 2015.

SUMMARY OF THE INVENTION

Problems to be Solved by the Invention

The present invention has been accomplished in view of the above-described prior art. An object of the present invention is to provide a method for detecting an index of an immune-related disease, which can rapidly and easily detect an objective index of the immune-related disease in a subject specimen; a method for assisting diagnosis of an immune-related disease, which can assist diagnosis by a doctor so that the doctor can rapidly and objectively diagnose the presence or absence of affection with the immune-related disease or prognosis of the immune-related disease; an examination kit for an immune-related disease, which can rapidly and easily examine the immune-related disease; a method for evaluating a suppression effect on an immune-related disease, which can rapidly and objectively evaluate the suppression effect on the immune-related disease in a subject treated for the immune-related disease or a subject administered with an immune-related disease inhibitor; a method for evaluating a test sample, which can objectively and accurately evaluate whether or not the test sample has an immune function-controlling action by simple operations; an immune function-controlling agent, which can control the immune function; and an agent for removing a primary cilium of an immune-related cell, which can remove a primary cilium of an immune-related cell.

Means for Solving the Problems

The present invention relates to:
(1) a method for detecting an index of an immune-related disease in a subject specimen collected from a subject, including the steps of: observing a primary cilium of an immune-related cell in the subject specimen,
comparing the resulting observations of the primary cilium of the immune-related cell in the subject specimen with observations of a primary cilium of an immune-related cell in a normal specimen, and
detecting a difference between the observations of the primary cilium of the immune-related cell in the subject specimen and the observations of the primary cilium of the immune-related cell in the normal specimen as an index of the immune-related disease;
(2) a method for assisting diagnosis of an immune-related disease in a subject, including the steps of:
observing a primary cilium of an immune-related cell in a subject specimen collected from the subject,
comparing the resulting observations of the primary cilium of the immune-related cell in the subject specimen with observations of a primary cilium of an immune-related cell in a specimen to be compared, and obtaining information for assisting diagnosis of the presence or absence of affection with the immune-related disease in the subject or information for assisting diagnosis of prognosis of the immune-related disease in the subject, on the basis of the resulting comparison result;
(3) an examination kit for an immune-related disease in a subject, including a specific binding substance against a primary cilium of an immune-related cell;
(4) a method for evaluating a suppression effect of a treatment applied to a subject affected with an immune-related disease or an immune-related disease inhibitor administered to the subject on an immune-related disease, including the steps of:
observing a primary cilium of an immune-related cell in a subject specimen collected from the subject before and after the treatment or before and after the administration of the immune-related disease inhibitor, and
comparing the resulting observations of the primary cilium of the immune-related cell in the subject specimen between before and after the treatment or between before and after the administration of the immune-related disease inhibitor with each other,
wherein change in the primary cilium of the immune-related cell in the subject specimen between before and after the treatment or between before and after the administration of the immune-related disease inhibitor is used as an index of the suppression effect on the immune-related disease;
(5) a method for evaluating a test sample, which is used for evaluating whether or not the test sample is a substance having an immune function-controlling action, including the steps of:

(A) observing a primary cilium of an immune-related cell in a cell group containing an immune-related cell having a primary cilium;

(B) contacting the cell group containing an immune-related cell having a primary cilium with the test sample, and observing the primary cilium of the immune-related cell in the cell group contacted with the test sample; and (C) evaluating whether or not the test sample is a substance having an immune function-controlling action on the basis of a difference between the resulting observations of the primary cilium of the immune-related cell in the cell group observed in the step (A) and the resulting observations of the primary cilium of the immune-related cell in the cell group observed in the step (B);

(6) an immune function-controlling agent for suppressing an immune function, including as an active ingredient an active substance for removing a primary cilium of an immune-related cell, the active substance having a function of removing a primary cilium from an immune-related cell having a primary cilium; and (7) an agent for removing a primary cilium of an immune-related cell, which is used for removing a primary cilium from an immune-related cell having a primary cilium, including as an active ingredient at least one kind selected from the group consisting of a steroid and a physiologically active substance.

Effects of the Invention

According to the present invention, there are provided a method for detecting an index of an immune-related disease, which can rapidly and easily detect an objective index of an immune-related disease in a subject specimen; a method for assisting diagnosis of an immune-related disease, which can assist diagnosis by a doctor so that the doctor can rapidly and objectively diagnose the presence or absence of affection with the immune-related disease or prognosis of the immune-related disease; an examination kit for an immune-related disease, which can rapidly and easily examine an immune-related disease; a method for evaluating a suppression effect on an immune-related disease, which can rapidly and objectively evaluate a suppression effect on an immune-related disease in a subject subjected to a treatment for the immune-related disease or a subject administered with an immune-related disease inhibitor; a method for evaluating a test sample, which can objectively and accurately evaluate whether or not the test sample has an immune function-controlling action by simple operations; an immune function-controlling agent, which can suppress an immune function; and an agent for removing a primary cilium of an immune-related cell, which can remove a primary cilium of an immune-related cell.

MODE FOR CARRYING OUT THE INVENTION

Figure 1A:
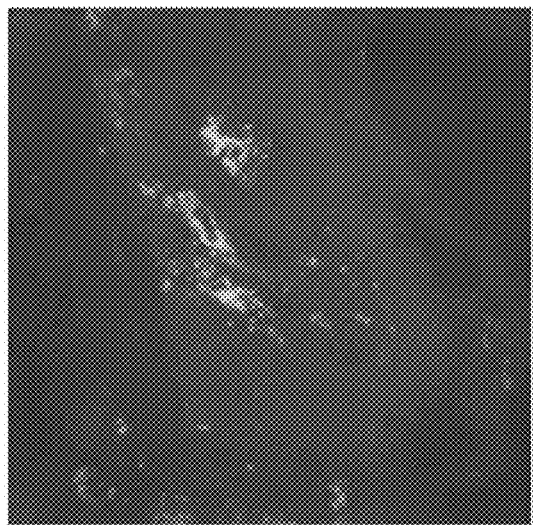
FIG. 1(A) is a photograph substituted for a drawing, showing a stained image of a human healthy skin tissue based on a Langerhans cell marker, examined in Example 1.

1. Method for Detecting Index of Immune-Related Disease

As described above, the method for detecting an index of an immune-related disease of the present invention is a method for detecting an index of an immune-related disease in a subject specimen collected from a subject, which is characterized in that the method includes the steps of: observing a primary cilium of an immune-related cell in the subject specimen;
  comparing the resulting observations of the primary cilium of the immune-related cell in the subject specimen with observations of a primary cilium of an immune-related cell in a normal specimen; and
  detecting a difference between the observations of the primary cilium of the immune-related cell in the subject specimen and the observations of the primary cilium of the immune-related cell in the normal specimen as an index of the immune-related disease.

According to the method for detecting an index of an immune-related disease of the present invention, an objective index of the immune-related disease in the subject specimen can be rapidly and easily detected, since a procedure including the steps of observing a primary cilium of an immune-related cell in a subject specimen and comparing observations of the primary cilium of the immune-related cell in the subject specimen with observations of a primary cilium of an immune-related cell in a normal specimen is adopted.

In the present specification, an "immune-related disease" refers to a disease of which symptom is appeared in connection with a function of an immune system. The immune-related disease includes, for example, tumor, immunodeficiency disease, infectious disease, autoimmune disease, rejection reaction associated with organ transplantation, allergic disease, inflammatory disease, or the like, and the present invention is not limited only to those exemplified ones.

The tumor includes, for example, tongue cancer, gingival cancer, malignant lymphoma, melanoma (malignant melanoma), maxillary cancer, nasal cancer, nasal cavity cancer, laryngeal cancer, pharyngeal cancer, glioma (for example, glioblastoma, astrocytoma, or the like), meningioma, neuroblastoma, thyroid papillary carcinoma, thyroid follicular carcinoma, medullary thyroid cancer, primary lung cancer, squamous cell cancer, adenocarcinoma, alveolar epithelial cancer, large cell anaplastic cancer, small cell anaplastic cancer, cartinoid, testicular tumor, prostate cancer, breast cancer (for example, papillary adenocarcinoma, comedocarcinoma, mucinous adenocarcinoma, medullary carcinoma, lobular carcinoma, scirrhous carcinosarcoma, metastatic tumor, or the like), mammary Paget's disease, breast sarcoma, bone tumor, thyroid cancer, gastric cancer, hepatoma, acute myeloid leukemia, acute promyelocytic leukemia, acute myelomonocytic leukemia, acute monocytic leukemia, acute lymphocytic leukemia, acute undifferentiated leukemia, chronic myeloid leukemia, chronic lymphocytic leukemia, adult T-cell leukemia, malignant lymphoma (for example, lymphosarcoma, reticulosarcoma, Hodgkin's disease, or the like), multiple myeloma, primary macroglobulinemia, childhood leukemia, esophageal cancer, gastric/colorectal leiomyosarcoma, gastric/intestinal malignant lymphoma, pancreatic/gallbladder cancer, duodenal cancer, colorectal cancer, primary hepatic cancer (for example, hepatoma, cholangiocarcinoma, or the like), hepatoblastoma, uterine carcinoma in situ, squamous cell carcinoma of the cervix, uterine adenocarcinoma, uterine adenosquamous carcinoma, adenocancroid of the uterine corpus, uterine sarcoma, uterine carcinosarcoma, uterine chorioadenoma destruens, uterine malignant chorioepithelioma, uterine malignant melanoma, ovarian cancer, mesodermal mixed tumor, renal cancer, renal cell carcinoma, transitional cell carcinoma of the renal pelvis, transitional cell cancer of the ureter, bladder papillary cancer, bladder transitional cell cancer, urethral squamous cell carcinoma, urethral adenocarcinoma, Wilms' tumor, rhabdomyosarcoma, fibrosarcoma, osteosarcoma, chondrosarcoma, synovial sarcoma, myxosarcoma, liposarcoma, Ewing's sarcoma, cutaneous squamous cell cancer, cutaneous basal cell cancer, cutaneous Bowen's disease, cutaneous Paget's disease, cutaneous malignant melanoma, malignant mesothelial cancer, metastatic adenocarcinoma, metastatic squamous cell cancer, metastatic sarcoma, mesothelioma (for example, pleural mesothelioma, peritoneal mesotheliomas, pericardial mesothelioma, or the like), or the like, and the present invention is not limited only to those exemplified ones.

The immunodeficiency disease includes, for example, acquired immunodeficiency syndrome (AIDS), severe combined immunodeficiency disease (SCID) associated with a severe disease (for example, cancer, aplastic anemia, leukemia, myelofibrosis, renal failure, diabetes, liver disease, splenic disease, or the like), common variable immunodeficiency, primary immunodeficiency syndrome, or the like, and the present invention is not limited only to those exemplified ones.

The infectious disease includes, for example, viral infection, pathogenic protozoan infection, bacterial infection, fungal infection, or the like, and the present invention is not limited only to those exemplified ones. The virus which causes viral infection includes, for example, a human hepatitis virus such as hepatitis A virus, hepatitis B virus, hepatitis C virus, or hepatitis E virus; a human immunodeficiency virus such as HIV1 or HIV2; a human T cell leukemia virus such as HTLV1 or HTLV2; a herpesvirus such as herpes simplex virus 1 or herpes simplex virus 2; Epstein-Barr virus; a cytomegalovirus; a varicella-zoster virus; a human herpesvirus such as human herpesvirus 6; a poliovirus; a measles virus; a rubella virus; Japanese encephalitis virus; a mumps virus; an influenza virus; a causative virus of a common cold syndrome such as an adenovirus, an enterovirus or a rhinovirus; a causative virus of a severe acute respiratory syndrome (SARS) such as a coronavirus; Ebola virus; West Nile virus; or the like, and the present invention is not limited only to those exemplified ones. A pathogenic protozoon causing pathogenic protozoan infection includes, for example, *Trypanosoma, Malaria, Toxoplasma*, or the like, and the present invention is not limited only to those exemplified ones. A bacterium causing bacterial infection includes, for example, *Mycobacterium, Salmonella, Listeria*, or the like, and the present invention is not limited only to those exemplified ones. The fungus causing fungal infection includes, for example, *Candida* or the like, and the present invention is not limited only to those exemplified ones.

The autoimmune disease includes, for example, arthritis, autoimmune hepatitis, autoimmune glomerulonephritis, autoimmune insulitis, autoimmune testitis, autoimmune ovaritis, ulcerative colitis, Sjogren's syndrome, Crohn's disease, Bechet's disease, Wegener's granulomatosis, hypersensitivity vasculitis, periarteritis nodosa, Hashimoto's disease, myxedema, Basedow's disease, Addison's disease, autoimmune hemolytic anemia, sudden thrombocytopenia, pernicious anemia, myasthenia gravis, demyelinating disease, aortitis syndrome, psoriasis, pemphigus, pemphigoid, collagenosis (for example, systemic lupus erythematosus, chronic rheumatoid arthritis, diffuse scleroderma, systemic progressive sclerosis, dermatomyositis, polyarteritis nodosa, rheumatic fever, or the like), Guillain-Barre syndrome, polyglandular autoimmune syndrome type II, primary biliary cirrhosis, vitiligo, type 1 diabetes, autoimmune thrombosis (for example, autoimmune arterial thrombosis, autoimmune venous thrombosis, or the like), habitual abortion, thrombocytopenia, antiphospholipid antibody syndrome, or the like, and the present invention is not limited only to those exemplified ones.

The rejection reaction associated with organ transplantation includes, for example, rejection reaction associated with renal transplantation, liver transplantation, heart transplantation, pulmonary transplantation, or the like; rejection reaction in bone marrow transplantation; graft-versus-host diseases; or the like, and the present invention is not limited only to those exemplified ones.

The allergic disease includes, for example, asthma, bronchial asthma, atopic dermatitis, urticaria, allergic rhinitis, allergic conjunctivitis, allergic gastroenteritis, anaphylactic shock, food allergies, or the like, and the present invention is not limited only to those exemplified ones.

The inflammatory disease includes, for example, dermatitis such as eczema, comedone, or contact dermatitis; colitis; vasculitis such as Takayasu's arteritis, giant cell arteritis (temporal arteritis), polyarteritis nodosa, Wegener's granulomatosis, Churg-Strauss syndrome (allergic granulomatous angiitis), allergic cutaneous vasculitis, Henoch-Schonlein purpura, hypersensitive angiitis, vasculitis syndrome, thromboangiitis obliterans (Buerger's disease), and nodular vasculitis; arthritis such as rheumatoid arthritis, chronic rheumatoid arthritis, deformans arthritis, tuberculous arthritis, septic arthritis, psoriatic arthritis, internal derangement of knee joint, idiopathic osteonecrosis, or osteoarthritis; hepatitis such as viral hepatitis or autoimmune hepatitis; nephritis such as acute glomerulonephritis, chronic nephritis, rapidly progressive nephritic syndrome, acute poststreptococcal glomerulonephritis, membranoproliferative glomerulonephritis, Goodpasture syndrome, mesangial proliferative glomerulonephritis (IgA nephropathy) or interstitial nephritis; gastritis such as acute infectious gastritis or chronic gastritis; pancreatitis, enteritis, laryngitis, neuritis, or the like, and the present invention is not limited only to those exemplified ones.

When the observations of a primary cilium of an immune-related cell having an antigen-presenting function are used in the method for detecting an index of an immune-related disease of the present invention, the observations can be suitably used for detection of each index of preferably an allergic disease, and more preferably atopic dermatitis, and asthma, among these immune-related diseases. In addition, when the observations of a primary cilium of an immune-related cell present in the skin is used in the method for detecting an index of an immune-related disease of the present invention, the observations can be suitably used for detection of each index of preferably an immune-related disease of the skin, and more preferably atopic dermatitis, psoriasis, eczema, and comedone, among these immune-related diseases.

An immune-related cell encompasses an immune cell which is mainly in charge of an immune reaction, and a cell of which main function is not an immune reaction but which possesses a function of indirectly being involved in an immune reaction, for example, a function of activation of an immune cell or the like (hereinafter referred to as an "immune function-possessing cell"). The immune cell includes, for example, a monocytic immune cell including a skin dendritic cell such as a Langerhans cell or a dermal dendritic cell; a lymphocytic immune cell such as T cell, NK cell, or B cell; a monocytic dendritic cell such as a conventional dendritic cell or plasmacytoid dendritic cell, or the like, and the present invention is not limited only to those exemplified ones. The immune function-possessing cell includes, for example, a cell which constitutes the skin tissue and which possesses a function of indirectly being involved in an immune reaction such as a keratinocyte, a fibroblast, or an epithelial cell, or the like, and the present invention is not limited only to those exemplified ones.

The immune-related cell to be used cannot be absolutely determined, because the immune-related cell to be used varies depending on the use application of the method for detecting an index of an immune-related disease of the present invention and the like. It is therefore preferred to determine the immune-related cell to be used in accordance with the use application of the method for detecting an index of an immune-related disease of the present invention, and the like. When the use application of the method for detecting an index of the immune-related disease of the present invention is detection of an index of an immune-related disease caused by an extracellular foreign substance such as a pathogen, a chemical substance, or a virus, among the immune-related cells, a cell which recognizes the extracellular foreign substance and initiates an immune reaction is preferable; a dendritic cell is more preferable; a skin dendritic cell and a monocyte dendritic cell are further preferable; and a monocyte dendritic cell is furthermore preferable. It is preferable that the immune-related cell is a primary immune-related cell, from the viewpoint of accurately detecting an index of an immune-related disease in a subject at an early stage.

In addition, in the present specification, a "primary cilium of an immune-related cell" refers to a primary cilium derived from an immune-related cell, which is present on the surface of the immune-related cell. The immune-related cell in a normal specimen has one or less primary cilium per cell.

First, in the method for detecting an index of an immune-related disease of the present invention, a primary cilium of an immune-related cell in a subject specimen collected from a subject is observed.

An observation item of a primary cilium includes, for example, the number of immune-related cells each having a primary cilium, the number of primary cilia per immune-related cell, the length of a primary cilium of an immune-related cell, the thickness of a primary cilium of an immune-related cell, and a combination of these items, or the like, and the present invention is not limited only to those exemplified ones. The observation item used for observation of the primary cilium of an immune-related cell cannot be absolutely determined, because a suitable observation item varies depending on the kind of the immune-related disease, the use application of the method for detecting an index of an immune-related disease of the present invention, and the like. It is therefore preferred to determine the observation item in accordance with the kind of the immune-related disease, the use application of the method for detecting an index of an immune-related disease of the present invention, and the like. When the method for detecting an index of an immune-related disease of the present invention is used for detecting an index of an immune-related disease in which the number of immune-related cells each having a primary cilium is increased, it is preferable that the number of immune-related cells each having a primary cilium is used as an observation item. The immune-related cell in a normal specimen has one or less primary cilium per cell. Accordingly, when an index of an immune-related disease in which the number of primary cilia per immune-related cell is increased is detected, it is preferable to use the number of primary cilia per immune-related cell as an observation item. When the method for detecting an index of the immune-related disease of the present invention is used for detecting an index of an immune-related disease in which the length of a primary cilium of an immune-related cell changes, it is preferable to use the length of the immune-related cell having an primary cilium as an observation item.

The subject includes, for example, a patient or an animal affected with an immune-related disease, a patient or an animal suspected to be affected with an immune-related disease, a healthy person, a healthy non-human animal, or the like, and the present invention is not limited only to those exemplified ones.

The subject specimen is a specimen to be tested, which is collected from a subject. The specimen includes, for example, blood, a skin tissue, a hair tissue including a dermal papilla cell, or the like, and the present invention is not limited only to those exemplified ones.

The observation item of the primary cilium of the immune-related cell in the subject specimen can be observed by, for example, contacting a sample containing the subject specimen with a specific binding substance against a primary cilium of an immune-related cell (hereinafter referred to as a "first specific binding substance") and detecting the first specific binding substance bound to the primary cilium of the immune-related cell, and the like.

The sample containing the subject specimen includes, for example, a fixed sample obtained by fixing a subject specimen with a fixing solution, or the like, and the present invention is not limited to those exemplified ones. The fixing solution includes, for example, acetone, methanol, a mixed solution of acetone and methanol, an aqueous formaldehyde solution, a phosphate buffer solution of formaldehyde, an aqueous paraformaldehyde solution, a phosphate-buffered saline solution of paraformaldehyde, a phosphate buffer solution of paraformaldehyde, or the like, and the present invention is not limited to those exemplified ones. The fixed sample can be washed with a washing solution or does not have to be washed. The washing solution includes, for example, phosphate-buffered saline or the like, and the present invention is not limited to those exemplified ones. When the first specific binding substance is a monoclonal antibody, a polyclonal antibody, or an antibody fragment, the fixed sample is preferably a sample blocked with a blocking agent, from the viewpoint of accurately observing the observation item of the primary cilium of the immune-related cell. The blocking agent includes, for example, phosphate-buffered saline containing albumin, phosphate buffer containing albumin, a blocking agent such as phosphate-buffered saline solution containing albumin and a surfactant, or the like, and the present invention is not limited to those exemplified ones.

The first specific binding substance includes, for example, a specific binding substance against a marker for a primary cilium of an immune-related cell, but the present invention is not limited to those exemplified ones. The marker for a primary cilium of an immune-related cell includes, for example, an ADP-ribosylation factor-like protein (Arl13b), acetylated tubulin, adenylate cyclase III, nephrocystin 3 (NPHP3), an intraflagellar transport protein (IFT88), somatostatin receptor 3 (sstr3), polycystin-1 (TRPC1), transient receptor potential vanilloid 4 (TRPV4), platelet-derived growth factor receptor α (PDGFR α), smoothened (Smo), or the like, and the present invention is not limited to those exemplified ones.

The specific binding substance against the marker for a primary cilium of an immune-related cell includes, for example, an antibody such as a monoclonal antibody or a polyclonal antibody; an antibody fragment such as a Fab fragment, a $F(ab')_2$ fragment, or a single-chain antibody, or the like, and the present invention is not limited to those exemplified ones. The monoclonal antibody can be obtained by, for example, culturing a hybridoma producing a monoclonal antibody against a marker for a primary cilium of an immune-related cell, to obtain a culture supernatant, and purifying the culture supernatant as occasion demands. The hybridoma can be produced by, for example, immunizing an animal by intravenously, subcutaneously or intraperitoneally administering the marker for a primary cilium of an immune-related cell to the animal, to give an antibody-producing cell, subjecting the antibody-producing cell and the myeloma cell to cell fusion, and culturing the obtained fusion cell in a HAT medium, and the like. The polyclonal antibody can be produced by, for example, immunizing an animal by intravenously, subcutaneously or intraperitoneally administering a marker for a primary cilium of an immune-related cell to the animal, to give an antiserum, and purifying the antiserum as occasion demands, and the like. The Fab fragment can be prepared by, for example, digesting a monoclonal antibody against a marker for a primary cilium of an immune-related cell with papain, and purifying the resulting papain digest as occasion demands, and the like. The $F(ab')_2$ fragment can be produced by, for example, digesting a monoclonal antibody against a marker for a primary cilium of an immune-related cell with pepsin, and purifying the pepsin digest as occasion demands, and the like. The single-chain antibody can be produced by introducing into a host cell a phagemid vector for expressing a single-chain antibody containing a nucleic acid construct in which a nucleic acid encoding a variable region of a light chain of a monoclonal antibody against a marker for a primary cilium of an immune-related cell, a nucleic acid encoding a linker, and a nucleic acid encoding a variable region of a heavy chain of the antibody are ligated together, expressing a polypeptide encoded by the nucleic acid construct in the host cell, and purifying the polypeptide as occasion demands, and the like.

Concrete examples of a specific binding substance for the marker for a primary cilium of an immune-related cell include an antibody against a primary cilium of an immune-related cell such as an anti-Arl13B antibody or an anti-acetylated tubulin antibody; an antibody fragment against a primary cilium of an immune-related cell; an aptamer against a primary cilium of an immune-related cell; and the like, and the present invention is not limited to those exemplified ones. Among these first specific binding substances, an antibody against a primary cilium of an immune-related cell is preferable, and an anti-Arl13B antibody and an anti-acetylated tubulin antibody are more preferable, from the viewpoint of accurately detecting a primary cilium of an immune-related cell. These first specific binding substances can be used alone or in combination of two or more kinds thereof.

When contacting the sample containing the subject specimen with the first specific binding substance, the first specific binding substance is used by being conjugated with a labeling substance for generating a detectable signal such as fluorescence or color, or used in combination with a label-specific binding substance which specifically binds to the first specific binding substance.

The labeling substance to be conjugated with the first specific binding substance includes, for example, a fluorescent substance such as fluorescein isothiocyanate, 2-(3-iminio-4,5-disulfonato-6-amino-3H-xanthene-9-yl)-5-[[5-(2,5-dioxo-3-pyrrolin-1-yl)pentyl]carbamoyl]benzoic acid (for example, manufactured by Invitrogen, trade name: Alexa Fluor 488, or the like), or 6-(2-carboxylato-4-carboxyphenyl)-1,2,10,11-tetrahydro-1,2,2,10,11-hexamethyl-4,8-bis(sulfomethyl)-1,11-diaza-13-oxoniapentacene (for example, manufactured by Invitrogen, trade name: Alexa Fluor 594, and the like); an enzyme such as peroxidase or alkaline phosphatase, or the like, and the present invention is not limited to those exemplified ones. Among these labeling substances, a fluorescent substance is preferable from the viewpoint of accurately detecting a primary cilium of an immune-related cell with high sensitivity.

The label-specific binding substance is usually a complex of a specific binding substance which specifically binds to a first specific binding substance bound to a primary cilium of an immune-related cell (hereinafter referred to as a "second specific binding substance") and a labeling substance. The second specific binding substance cannot be absolutely determined, because the second specific binding substance varies depending on the kind of the first specific binding substance and the like. It is therefore preferred to determine the second specific binding substance in accordance with the kind of the first specific binding substance and the like. The labeling substance used for the label-specific binding substance is the same as the labeling substance to be conjugated with the first specific binding substance.

The method for contacting the sample containing the subject specimen with the first specific binding substance cannot be absolutely determined, because the method for contacting the sample containing the subject specimen with the first specific binding substance varies depending on the kind of the first specific binding substance, the kind of the means for detecting the specific binding substance bound to a primary cilium of an immune-related cell, the kind of the subject specimen, and the like. It is therefore preferred to determine the method for contacting the sample containing the subject specimen with the first specific binding substance in accordance with the kind of the first specific binding substance, the kind of the means for detecting the specific binding substance bound to a primary cilium of an immune-related cell, the kind of the subject specimen, and the like. It is preferable that the contact between the sample containing the subject specimen is usually contacted with the first specific binding substance in a liquid phase, since the operations are easy. The liquid phase cannot be absolutely determined because the liquid phase varies depending on the kind of the first specific binding substance, the kind of the means for detecting the specific binding substance bound to a primary cilium of an immune-related cell, and the like. It is therefore preferred to determine the liquid phase in accordance with the kind of the first specific binding substance, the kind of the means for detecting a specific binding substance bound to a primary cilium of an immune-related cell, and the like.

When the sample containing the subject specimen is contacted with the first specific binding substance, the mixing ratio of the sample containing the subject specimen and the first specific binding substance and the contact time thereof cannot be absolutely determined, because the mixing ratio and the contact time vary depending on the kind of the subject specimen, the kind of the first specific binding substance, and the like. It is therefore preferred to appropriately set the mixing ratio and the contact time in accordance with the kind of the subject specimen, the kind of the first specific binding substance, and the like.

From the viewpoint of accurately observing the observation item of a primary cilium of an immune-related cell, it is preferable to wash the sample containing the subject specimen after the contact of the first specific binding substance with an appropriate washing solution. The washing solution includes, for example, phosphate-buffered saline, phosphate buffer, phosphate-buffered saline solution containing a surfactant, or the like, and the present invention is not limited to those exemplified ones.

The first specific binding substance bound to a primary cilium of an immune-related cell can be detected by detecting a signal derived from a labeling substance conjugated with a first specific binding substance bound to a primary cilium of an immune-related cell, when the first specific binding substance is used in a state of being conjugated with the labeling substance upon contacting the sample containing the subject specimen with the first specific binding substance. In addition, when the first specific binding substance is used in combination with the label-specific binding substance upon contacting the sample containing the subject specimen with the first specific binding substance, the first specific binding substance bound to a primary cilium of an immune-related cell can be detected by detecting a signal derived from the labeling substance of the label-specific binding substance used in combination with the first specific binding substance.

When the number of immune-related cells each having a primary cilium is used as an observation item of a primary cilium of an immune-related cell, the number of immune-related cells each having a primary cilium can be examined by, for example, counting the number of immune-related cells in which a signal derived from a labeling substance is detected, and the like. When the number of primary cilia per immune-related cell is used as an observation item of a primary cilium of an immune-related cell, the number of primary cilia per immune-related cell can be examined by, for example, counting the number of primary cilia in which a signal derived from a labeling substance is detected per immune-related cell, and the like. When the length of a primary cilium of an immune-related cell is used as the observation item of the primary cilium of the immune-related cell, the length of the primary cilium of the immune-related cell can be examined by, for example, imaging the signal derived from the labeling substance and measuring the length from the end in the length direction to the other end of the portion in which the signal is generated in the obtained image, and the like.

The means for detecting a signal includes, for example, an optical microscope such as a fluorescence microscope or a confocal laser microscope; an image analyzer such as a fluorescence imaging analyzer; a flow cytometer such as a fluorescence flow cytometer or an imaging flow cytometer, or the like, and the present invention is not limited to those exemplified ones.

In the method for detecting an index of an immune-related disease of the present invention, the kind of the immune-related cell can be identified as occasion demands. When the kind of immune cell is identified, an identification reagent for identifying the kind of immune cell can be used. The reagent for identifying the kind of the immune cell includes, for example, an antibody against a marker corresponding to the kind of the immune cell, concretely, an anti-CD1a antibody, an anti-CD14 antibody, an anti-CD3 antibody, an anti-CD20 antibody, an anti-CD4 antibody, an anti-CD8 antibody, an anti-CD56 antibody, an anti-langerin antibody, an anti-CD205 antibody, an anti-CD11C antibody, an anti-CD123 antibody, an anti-HLA-DR antibody, or the like, and the present invention is not limited to those exemplified ones. The marker corresponding to the kind of the immune cell includes, for example, a Langerhans cell marker such as langerin (CD207), CD1a or CD205; a monocytic dendritic cell marker such as CD11c, CD123 or HLA-DR; or the like, and the present invention is not limited to those exemplified ones. In addition, when the kind of the immune function-possessing cell is identified, an identification reagent for identifying the kind of the immune function-possessing cell can be used. The reagent for identifying the kind of the immune function-possessing cell includes, for example, an antibody against a marker corresponding to the kind of the immune function-possessing cell, concretely, an anti-keratin-1 antibody, an anti-keratin-10 antibody, an anti-involucrin antibody, an anti-alpha-smooth muscle actin antibody, an anti-vimentin antibody, an anti-cytokeratin antibody, or an anti-E-cadherin antibody, or the like, and the present invention is not limited to those exemplified ones. The marker corresponding to the kind of the immune function-possessing cell includes, for example, a keratinocyte marker such as keratin-1, keratin-10, or involucrin; a fibroblast marker such as an alpha-smooth muscle actin antibody or vimentin; an epithelial cell marker such as cytokeratin or E-cadherin; or the like, and the present invention is not limited to those exemplified ones.

Next, the resulting observations of the primary cilium of the immune-related cell in the subject specimen is compared with the observations of the primary cilium of the immune-related cell in the normal specimen, and a difference between the observations of the primary cilium of the immune-related cell in the subject specimen and the observations of the primary cilium of the immune-related cell in the normal specimen is detected as an index of the immune-related disease.

The normal specimen includes, for example, a specimen collected from a healthy person or a healthy non-human animal, a specimen collected from a non-lesion part of the subject, or the like, and the present invention is not limited to those exemplified ones. When blood collected from a subject is used as the subject specimen, among these normal specimens, blood collected from a healthy person or a healthy non-human animal is preferable, from the viewpoint of accurately detecting the index of the immune-related disease. When a skin tissue collected from a subject is used as the subject specimen, the normal specimen can be a skin tissue collected from a healthy person or a healthy non-human animal, or can be a skin tissue collected from a non-lesion part of the subject. When a hair tissue collected from a subject is used as the subject specimen, the normal specimen can be a hair tissue collected from a healthy person or a healthy non-human animal, or can be a hair tissue collected from a non-lesion part of the subject.

The immune-related cell in the normal specimen includes, for example, an immune-related cell in a normal specimen of the same kind as that of the subject specimen collected from the same subject as the subject from which the subject was collected, an immune-related cell in a normal specimen of the same kind as the subject specimen collected from a healthy person or a healthy non-human animal, or the like, and the present invention is not limited to those exemplified ones. The observations of the primary cilium of the immune-related cell in the normal specimen can be observations obtained by observing the primary cilium of the immune-related cell of the normal specimen in the same manner as in the observation of the primary cilium of an immune-related cell in the subject specimen, or can be accumulated data of known observations related to the normal specimen. In addition, the observation item used for the observations of the primary cilium of the immune-related cell in the normal specimen is the same as observation item used for the observations of the primary cilium of the immune-related cell in the subject specimen.

A method for comparing observations of the primary cilium of the immune-related cell between the subject specimen and the normal specimen includes, for example, a method of comparing the number of immune-related cells each having a primary cilium between the subject specimen and the normal specimen, a method of comparing the number of primary cilia per immune-related cell between the subject specimen and the normal specimen, a method of comparing the length of the primary cilium of the immune-related cell between the subject specimen and the normal specimen, or the like, and the present invention is not limited to those exemplified ones.

A method for comparing the number of immune-related cells each having a primary cilium between the subject specimen and the normal specimen includes, for example, a method of directly comparing the number of immune-related cells each having a primary cilium in the subject specimen with the number of immune-related cells each having a primary cilium in the normal specimen, and a method of comparing the formation rate of a primary cilium of the immune-related cell in the test specimen calculated on the basis of the number of immune-related cells each having a primary cilium in the subject specimen and the formation rate of a primary cilium of the immune-related cell in the normal specimen calculated on the basis of the number of immune-related cells each having a primary cilium in the normal specimen, or the like, and the present invention is not limited to those exemplified ones. When the normal specimen is a specimen collected from a healthy person or a healthy non-human animal, an average value calculated from the number of immune-related cells each having a primary cilium in each specimen collected from a plurality of healthy persons or a plurality of healthy non-human animals can be used as the number of immune-related cells each having an primary cilium in the normal specimen.

The formation rate of a primary cilium of the immune-related cell in the subject specimen or the normal specimen can be calculated on the basis of the formula (I):

[Formation rate of primary cilium of immune-related cell in specimen]=[(Number of immune-related cells each having primary cilium in specimen)/(Number of total immune–related cells in specimen)]×100 (I)

wherein "specimen" indicates a subject specimen or a normal specimen.

A method for comparing the number of primary cilia per immune-related cell between the subject specimen and the normal specimen includes, for example, a method of directly comparing the number of primary cilia per immune-related cell in the subject specimen with the number of primary cilia per immune-related cell in the normal specimen, or the like, and the present invention is not limited to those exemplified ones. When the normal specimen is a specimen collected from a healthy person or a healthy non-human animal, an average value calculated from the number of primary cilia per immune-related cell in each specimen collected from a plurality of healthy persons or a plurality of healthy non-human animals can be used as the number of primary cilia per immune-related cell in the normal specimen.

A method for comparing the length of the primary cilium of an immune-related cell between the subject specimen and the normal specimen includes, for example, a method of directly comparing the length of the primary cilium of the immune-related cell in the subject specimen with the length of the primary cilium of the immune-related cell in the normal specimen for comparison, or the like, and the present invention is not limited to those exemplified ones. When the normal specimen is a specimen collected from a healthy person or a healthy non-human animal, an average value calculated from the length of the primary cilium of the immune-related cell in each specimen collected from a plurality of healthy persons or a plurality of healthy non-human animals can be used as the length of the primary cilium of the immune-related cell in the normal specimen.

When the immune-related cells is an immune-related cell present in blood, it is preferred that by using blood as a subject specimen, the formation rate of the primary cilium of the immune-related cell in the subject specimen is compared with the formation rate of the primary cilium of the immune-related cell in the normal specimen, and that a difference between the formation rate of the primary cilium of the immune-related cell in the subject specimen and the formation rate of the primary cilium of the immune-related cell in the normal specimen is used as an index of the immune-related disease, from the viewpoint of reducing the invasion degree to the subject and observing a wide variety of and a number of primary cilia of an immune-related cell at the same time. In addition, when the immune-related cell is an immune-related cells present in the epidermis, it is preferred that by using the epidermal tissue as a subject specimen, the number of immune-related cells each having a primary cilium in the subject specimen is compared with the number of immune-related cells each having a primary cilium in the normal specimen, and that a difference between the number of immune-related cells each having a primary cilium in the subject specimen and the number of immune-related cells each having an primary cilium in the normal specimen is used as an index of the immune-related disease, from the viewpoint of rapidly and accurately detecting the index of the immune-related disease.

When there is at least one kind of difference selected from the group consisting of the following differences A to C between a subject specimen and a normal specimen, the difference is used as an index of an immune-related disease.
<Difference A>
A difference between the number of immune-related cells each having a primary cilium in the subject specimen and the number of immune-related cells each having a primary cilium in the normal specimen
<Difference B>
A difference between the number of primary cilia per immune-related cell in the subject specimen and the number of primary cilia per immune-related cell in the normal specimen
<Difference C>
A difference between the length of a primary cilium of an immune-related cell in the subject specimen and the length of a primary cilium of an immune-related cell in the normal specimen The method for detecting an index of an immune-related disease of the present invention can be applied to an immune-related disease caused by an abnormal increase in the number of immune-related cells each having a primary cilium, an abnormal increase in the formation rate of a primary cilium of an immune-related cell, abnormal elongation of the length of a primary cilium of an immune-related cell, or the like (hereinafter referred to as "immune-related disease A"). The index of the immune-related disease A includes, for example, the following index A, index B, index C, or the like, and the present invention is not limited to those exemplified ones. These indices can be used alone or in combination.
<Index A>
The number of immune-related cells each having a primary cilium in the subject specimen being significantly larger than the number of immune-related cells each having a primary cilium in the normal specimen.
<Index B>
The formation rate of a primary cilium of an immune-related cell in the subject being significantly higher than the formation rate of a primary cilium of an immune-related cell in the normal specimen.
<Index C>
The length of a primary cilium of an immune-related cell in the subject specimen being significantly longer than the length of a primary cilium of an immune-related cell in the normal specimen.

In addition, the method for detecting an index of an immune-related disease of the present invention can be applied to an immune-related disease caused by an abnormal decrease in the number of immune-related cells each having a primary cilium, and an abnormal decrease in the formation rate of a primary cilium of an immune-related cell, or the like (hereinafter referred to as an "immune-related disease B"). An index of the immune-related disease B includes the following index D, index E, or the like, and the present invention is not limited to those exemplified ones. These indices can be used alone or in combination.

<Index D>

The number of immune-related cells each having a primary cilium in the subject specimen being significantly smaller than the number of immune-related cells each having a primary cilium in the normal specimen.

<Index E>

The formation rate of a primary cilium of an immune-related cell in a subject being significantly smaller than the formation rate of a primary cilium of an immune-related cell in a normal specimen.

The immune-related disease A includes, for example, allergic asthma, atopic dermatitis, or the like, and the present invention is not limited to those exemplified ones. The immune-related disease B includes, for example, glioblastoma, renal cell cancer, melanoma (malignant melanoma), or the like, and the present invention is not limited to those exemplified ones.

As described above, according to the method for detecting an index of an immune-related disease of the present invention, an objective index of an immune-related disease in a subject specimen can be detected rapidly and easily. Accordingly, the method for detecting an index of an immune-related disease of the present invention is expected to be used for development of an immune-related disease inhibitor or a therapeutic agent, examination of an immune-related disease in an examination institution, a test department of a medical institution, or the like, diagnosis of the presence or absence of affection with an immune-related disease or prognosis of an immune-related disease by a doctor in a medical institution, and the like.

2. Method for Assisting Diagnosis of Immune-Related Disease

A method for assisting diagnosis of an immune-related disease of the present invention is a method for assisting diagnosis of an immune-related disease in a subject, including the steps of:

observing a primary cilium of an immune-related cell in a subject specimen collected from a subject, comparing the resulting observations of the primary cilium of an immune-related cell in the subject specimen with observations of a primary cilium of an immune-related cell in a subject specimen to be compared, and obtaining information for assisting diagnosis of the presence or absence of affection with an immune-related disease in the subject or information for assisting diagnosis of prognosis of an immune-related disease in the subject on the basis of the obtained comparison results.

According to the method for assisting diagnosis of an immune-related disease of the present invention, a procedure including the steps of comparing the observations of the primary cilium of the immune-related cell in the subject specimen with the observations of the primary cilium of the immune-related cell in the specimen to be compared, and obtaining information for assisting diagnosis of the presence or absence of affection with an immune-related disease in the subject or information for assisting diagnosis of prognosis of an immune-related disease in the subject on the basis of the obtained comparison results is adopted. Accordingly, an objective basis for decision for diagnosing that the subject is affected with the immune-related disease or that the subject is not affected with the immune-related disease, or diagnosing that the prognosis of the immune-related disease in the subject is good or that the prognosis of the immune-related disease in the subject is poor can be obtained. Thus, according to the method for assisting diagnosis of an immune-related disease of the present invention, diagnosis can be assisted so that a doctor can rapidly and objectively diagnose the presence or absence of affection with the immune-related disease or the prognosis of the immune-related disease.

When the method for assisting diagnosis of an immune-related disease of the present invention is used for assisting diagnosis of the presence or absence of affection with an immune-related disease, the subject includes, for example, a patient or an animal suspected to be affected with an immune-related disease, a healthy person, a healthy non-human animal, or the like, and the present invention is not limited to those exemplified ones. In addition, when the method for assisting diagnosis of an immune-related diseases of the present invention is used for assisting diagnosis of prognosis of an immune-related disease, the subject includes, for example, a patient or a subject before and after treatment affected with an immune-related disease, a healthy person, a healthy non-human animal, or the like, and the present invention is not limited to those exemplified ones.

The subject specimen is the same as the subject specimen used in the method for detecting an index of an immune-related disease. A primary cilium of an immune-related cell in a subject specimen can be observed in the same manner as in the observation of the primary cilium of the immune-related cell in the subject specimen performed in the method for detecting an index of an immune-related disease. Comparison of observations of a primary cilium of an immune-related cell between the subject specimen and a specimen to be compared can be performed in the same manner as in the comparison of observations of the primary cilium of the immune-related cell between the subject specimen and the normal specimen in the method for detecting an index of an immune-related disease, except that a specimen to be compared is used in place of a normal specimen in a method of detecting an index of an immune-related disease. In addition, the observation item used upon observing the primary cilium of the immune-related cell is the same as the observation item in the method for detecting an index of an immune-related disease.

When there is at least one kind of difference selected from the group consisting of the following differences a to c between a subject specimen and a specimen to be compared, it is possible to obtain information for assisting diagnosis used for a basis for decision for diagnosing the presence or absence of affection with an immune-related disease in the subject or prognosis of an immune-related disease in the subject on the basis of the difference.

<Difference a>

A difference between the number of immune-related cells each having a primary cilium in the subject and the number of immune-related cells each having a primary cilium in the specimen to be compared <Difference b>

A difference between the number of primary cilia per immune-related cell in the subject specimen and the number of primary cilia per immune-related cell in the specimen to be compared <Difference c>

A difference between the length of a primary cilium of an immune-related cell in the subject specimen and the length of a primary cilium of an immune-related cell in the specimen to be compared When the method for assisting diagnosis of an immune-related disease of the present invention is used for assisting diagnosis of the presence or absence of affection with an immune-related disease, a normal specimen is used as a specimen to be compared. The normal specimen is the same as the normal specimen used in the method for detecting an index of an immune-related disease. In addition, when the method for assisting diagnosis of an immune-related disease of the present invention is used for assisting diagnosis of prognosis of an immune-related disease, the same kind of specimen (hereinafter referred to as a "untreated specimen") collected from an untreated subject is used as a specimen to be compared.

When the method for assisting diagnosis of an immune-related disease of the present invention is used for assisting diagnosis of the presence or absence of affection with the immune-related disease A, information for assisting diagnosis used as a basis for decision for a doctor to diagnose that the subject is affected with the immune-related disease can be obtained from at least one comparison result selected from the group consisting of the following comparison result A, comparison result B and comparison result C.
<Comparison Result A>
A comparison result indicating that the number of immune-related cells each having a primary cilium in the subject specimen is significantly larger than the number of immune-related cells each having a primary cilium in the normal specimen as the specimen to be compared
<Comparison Result B>
A comparison result indicating that the formation rate of a primary cilium of an immune-related cell in the subject specimen is significantly higher than the formation rate of a primary cilium of an immune-related cell in the normal specimen as the specimen to be compared
<Comparison Result C>
A comparison result indicating that the length of a primary cilium of an immune-related cell in the subject specimen is significantly longer than the length of a primary cilium of an immune-related cell in the normal specimen as the specimen to be compared In addition, when the method for assisting diagnosis of an immune-related disease of the present invention is used for assisting diagnosis of the presence or absence of affection with the immune-related disease B, information for assisting diagnosis used as a basis for decision for a doctor to diagnose that the subject is affected with the immune-related disease can be obtained from at least one comparison result selected from the group consisting of the following comparison result D and comparison result E.
<Comparison Result D>
A comparison result indicating that the number of immune-related cells each having a primary cilium in the subject specimen is significantly smaller than the number of immune-related cells each having a primary cilium in the normal specimen as the specimen to be compared
<Comparison Result E>
A comparison result indicating that the formation rate of a primary cilium of an immune-related cell in the subject specimen is significantly lower than the formation rate of a primary cilium of an immune-related cell in the normal specimen as the specimen to be compared On the other hand, when a comparison result indicating that there is no difference between the subject specimen and the normal specimen as the specimen to be compared is obtained, information for assisting diagnosis used as a basis for decision for a doctor to diagnose that the subject is not affected with the immune-related disease can be obtained from the comparison result.

When the method for assisting diagnosis of an immune-related disease of the present invention is used for assisting diagnosis of prognosis of the immune-related disease A in a subject, information for assisting diagnosis used as a basis for decision for a doctor to diagnose that the prognosis of the immune-related disease A is good in the subject can be obtained from at least one comparison result selected from the group consisting of the following comparison result a-1, comparison result b-1, and comparison result c-1. In addition, information for assisting diagnosis used as a basis for decision for a doctor to diagnose that the prognosis of the immune-related disease A is poor in the subject can be obtained from at least one comparison result selected from the group consisting of the following comparison result a-2, comparison result b-2, and comparison result c-2.
(Information for Assisting Diagnosis of Good Prognosis)
<Comparison Result a-1>
A comparison result indicating that the number of immune-related cells each having a primary cilium in the subject specimen after treatment is significantly smaller than the number of immune-related cells each having a primary cilium in the untreated specimen as the specimen to be compared
<Comparison Result b-1>
A comparison result indicating that the formation rate of a primary cilium of an immune-related cell in the subject specimen after treatment is significantly lower than the formation rate of a primary cilium of an immune-related cell in the untreated specimen as the specimen to be compared
<Comparison Result c-1>
A comparison result indicating that the length of a primary cilium of an immune-related cell in the subject specimen after treatment is significantly shorter than the length of a primary cilium of an immune-related cell in the untreated specimen as the specimen to be compared
(Information for Assisting Diagnosis of Poor Prognosis)
<Comparison Result a-2>
A comparison result indicating that the number of immune-related cells each having a primary cilium in the subject specimen after treatment is the same as the number of immune-related cells each having a primary cilium in the untreated specimen as the specimen to be compared or larger than the number of immune-related cells each having a primary cilium in the untreated specimen
<Comparison Result b-2>
A comparison result indicating that the formation rate of a primary cilium of an immune-related cell in the subject specimen after treatment is the same as the formation rate of a primary cilium of an immune-related cell in the untreated specimen as the specimen to be compared or higher than the formation rate of a primary cilium of an immune-related cell in the untreated specimen
<Comparison Result c-2>
A comparison result indicating that the length of a primary cilium of an immune-related cell in the subject specimen after treatment is the same as the length of a primary cilium of an immune-related cell in the untreated specimen as the specimen to be compared or longer than the length of the primary cilium of an immune-related cell in the untreated specimen When the method for assisting diagnosis of an immune-related disease of the present invention is used for diagnosing prognosis of the immune-related disease B in a subject, information for assisting diagnosis used as a basis for decision for a doctor to diagnose that the prognosis of the immune-related disease B is good in the subject can be obtained from at least one comparison result selected from the group consisting of the following comparison result e-1 and comparison result f-1. In addition, information for assisting diagnosis used as a basis for decision for a doctor to diagnose that the prognosis of the immune-related disease B is poor in the subject can be obtained from at least one comparison result selected from the group consisting of the following comparison result e-2 and comparison result f-2.
(Information for Assisting Diagnosis of Good Prognosis)
<Comparison Result e-1>
A comparison result indicating that the number of immune-related cells each having a primary cilium in the subject after treatment is significantly larger than the number of immune-related cells each having a primary cilium in the untreated specimen as the specimen to be compared
<Comparison Result f-1>
A comparison result indicating that the formation rate of a primary cilium of an immune-related cell in the subject after treatment is significantly higher than the formation rate of a primary cilium of an immune-related cell in the untreated specimen as the specimen to be compared
(Information for Assisting Diagnosis of Poor Prognosis)
<Comparison Result e-2>
A comparison result indicating that the number of immune-related cells each having a primary cilium in the subject specimen after treatment is the same as the number of immune-related cells each having a primary cilium in the untreated specimen or smaller than the number of immune-related cells each having a primary cilium in the untreated specimen
<Comparison Result f-2>
A comparison result indicating that the formation rate of a primary cilium of an immune-related cell in the subject specimen after treatment is the same as the formation rate of a primary cilium of an immune-related cell in the untreated specimen or lower than the formation rate of a primary cilium of an immune-related cell in the untreated specimen Accordingly, in the method for assisting diagnosis of an immune-related disease of the present invention, the kind of the immune-related cell can be identified as occasion demands. When the kind of the immune-related cell is identified, an identification reagent for identifying the kind of the immune-related cell can be used. The identification reagent used in the method for assisting diagnosis of an immune-related disease of the present invention is the same as the identification reagent used in the method for detecting an index of an immune-related disease.

As described above, according to the method for assisting diagnosis of an immune-related disease of the present invention, since an objective basis for decision for diagnosing that the subject is affected with the immune-related disease or the subject is not affected with the immune-related disease can be obtained, the diagnosis can be assisted so that a doctor can rapidly and objectively diagnose the presence or absence of affection with of the immune-related disease in the subject. In addition, according to the method for assisting diagnosis of an immune-related disease of the present invention, since an objective basis for decision for diagnosing that prognosis of the immune-related disease in the subject is good or prognosis of the immune-related disease in the subject is poor can be obtained, the diagnosis can be assisted so that a doctor can rapidly and objectively diagnose prognosis of the immune-related disease in the subject. Accordingly, the method for assisting diagnosis of an immune-related disease of the present invention is expected to be used for examination of an immune-related disease in an examination organization, a test department of a medical institution, diagnosis of the presence or absence of affection with an immune-related disease or diagnosis of prognosis of an immune-related disease by a doctor in a medical institution, or the like.

3. Examination Kit for Immune-Related Disease

The kit for examining an immune-related disease of the present invention is a kit for examining an immune-related disease in a subject, which is characterized in that the kit includes a first specific binding substance.

Since the examination kit for an immune-related disease of the present invention includes the first specific binding substance, according to the examination kit for an immune-related disease of the present invention, the presence or absence of a primary cilium of an immune-related cell in a subject specimen collected from a subject can be rapidly and easily examined. Thus, according to the examination kit for an immune-related disease of the present invention, an immune-related disease can be rapidly and easily examined.

The first specific binding substance used in the examination kit for an immune-related disease of the present invention is the same as the first specific binding substance used in the method for detecting an index of an immune-related disease. The first specific binding substance can be conjugated with a labeling substance, or does not have to be conjugated with a labeling substance. The labeling substance conjugated with the first specific binding substance is the same as the labeling substance used in the method for detecting an index of an immune-related disease.

When the first specific binding substance is not conjugated with the labeling substance, the examination kit for an immune-related disease of the present invention can include a label-specific binding substance which specifically binds to the first specific binding substance. The label-specific binding substance is the same as the label-specific binding substance used in the method for detecting an index of an immune-related disease.

The examination kit for an immune-related disease of the present invention can include an identification reagent for identifying the kind of an immune-related cell; a reagent for preparing a sample used for the examination such as a fixing solution, a washing solution, or a blocking agent; a buffer for binding reaction; or the like. The identification reagent is the same as the identification reagent used in the method for detecting an index of an immune-related disease. The fixing solution, the washing solution, and the blocking agent are the same as the fixing solution, the washing solution, and the blocking agent used in the method for detecting an index of an immune-related disease. The buffer for binding reaction cannot be absolutely determined, because the buffer for binding reaction varies depending on the kind of the first specific binding substance, the kind of the labeling substance used for detection of the first specific binding substance, the kind of the label-specific binding substance, and the like. It is therefore preferred to determine the buffer for binding reaction in accordance with the kind of the first specific binding substance, and the like.

The first specific binding substance can be enclosed in a container including a buffer for storage containing a stabilizing agent such as glycerol, ethylene glycol, bovine serum albumin, 2-mercaptoethanol, dithiothreitol, or ethylene diamine tetraacetic acid, and can be enclosed in a container in a freeze-dried state. The buffer for storage includes a buffer having a pH in accordance with the pH stability of the first specific binding substance. The fixing solution, the washing solution, and the blocking agent are usually enclosed in a container different from the container including the first specific binding substance.

As described above, according to the examination kit for an immune-related disease of the present invention, an immune-related disease can be examined rapidly and easily, since the examination kit for an immune-related disease of the present invention includes the first specific binding substance. Accordingly, the examination kit for an immune-related disease of the present invention is expected to be used for development of an immune-related disease inhibitor or a therapeutic agent, an examination of an immune-related disease in an examination organization, a test department of a medical institution, and the like, diagnosis of an immune-related disease by a doctor in a medical institution, and the like.

4. Method for Evaluating Suppression Effect on Immune-Related Disease

The method for evaluating a suppression effect on an immune-related disease is a method for evaluating a suppression effect of a treatment applied to a subject affected with an immune-related disease or an immune-related disease inhibitor administered to the subject on an immune-related disease, which is characterized in that the method includes the steps of:

observing a primary cilium of an immune-related cell in a subject specimen before and after the treatment or administration with the immune-related disease inhibitor collected from the subject, comparing observations of the primary cilium of an immune-related cell in the subject specimen between before and after the treatment or between before and after the administration with the immune-related disease inhibitor, wherein change in the primary cilium of an immune-related cell in the subject specimen between before and after the treatment or between before and after the administration with the immune-related disease inhibitor is used as an index of the suppression effect on the immune-related disease.

According to the method for evaluating an inhibitory effect on an immune-related disease of the present invention, the suppression effect on the immune-related disease in the subject subjected to the treatment of the immune-related disease administered with the immune-related disease inhibitor can be evaluated rapidly and objectively, since change in the primary cilium of the immune-related cell in the subject specimen between before and after treatment or between before and after administration of an immune-related disease inhibitor is used as an index of the inhibitory effect on the immune-related disease.

The treatment includes, for example, a drug therapy using a therapeutic agent for an immune-related disease such as a steroid; a food therapy; or the like, and the present invention is not limited to those exemplified ones. In addition, in the present specification, the "immune-related disease inhibitor" refers to a quasi-drug and a cosmetic component.

The observation item used upon observing the primary cilium of an immune-related cell is the same as the observation item in the method for detecting an index of an immune-related disease. The subject is the same as the subject used in the method for detecting an index of an immune-related disease. The subject specimen is the same as the subject specimen used in the method for detecting an index of an immune-related disease, except that the subject specimen is a subject specimen before and after treatment or before and after administration. Additionally, in the following, a subject specimen before administration of an immune-related disease inhibitor is referred to as a "pre-administration specimen", and a subject specimen after administration of an immune-related disease inhibitor is referred to as a "post-administration specimen".

Observation of the primary cilium of the immune-related cell in the subject specimen and comparison of the observations of the primary cilium of the immune-related cell in the subject specimen between before and after treatment or between before and after administration with an immune-related disease inhibitor can be performed in the same manner as those in the comparison of the observations of the primary cilium of the immune-related cell between the subject specimen and the normal specimen in the method for detecting an index of an immune-related disease.

Change in the primary cilium of an immune-related cell in the subject specimen between before and after treatment is used as an index of a suppression effect of the treatment on an immune-related disease.

When the immune-related disease is the immune-related disease A, the presence or absence of the inhibitory effect of the treatment on the immune-related disease is evaluated based on the following "evaluation criteria for having an effect" and "evaluation criteria for no effect". The items A-1 to A-3 of "evaluation criteria for having an effect" can be used alone or in combination. The items B-1 to B-3 of "evaluation criteria for no effect" can be used alone or in combination.

<Evaluation Criteria for Having an Effect>

A-1: the number of immune-related cells each having a primary cilium in the subject specimen after treatment being significantly smaller than the number of immune-related cells each having a primary cilium in the untreated specimen A-2: the formation rate of a primary cilium of the immune-related cell in the subject specimen after treatment being significantly lower than the formation rate of a primary cilium of the immune-related cell in the untreated specimen A-3: the length of the primary cilium of the immune-related cell in the subject specimen after treatment being significantly shorter than the length of the primary cilium of the immune-related cell in the untreated specimen <Evaluation Criteria for No Effect>

B-1: the number of immune-related cells each having a primary cilium in a subject specimen after treatment being the same as the number of immune-related cells each having a primary cilium in an untreated specimen, or being significantly larger than the number of immune-related cells each having a primary cilium in an untreated specimen B-2: the formation rate of a primary cilium of an immune-related cell in a subject specimen after treatment being the same as the formation rate of the primary cilium of an immune-related cell in the untreated specimen, or being significantly higher than the formation rate of a primary cilium of an immune-related cell in the untreated specimen B-3: the length of a primary cilium of an immune-related cell in a subject specimen after treatment being the same as the length of the primary cilium of an immune-related cell in the untreated specimen, or being significantly longer than the length of a primary cilium of an immune-related cell in the untreated specimen.

When the immune-related disease is the immune-related disease B, the presence or absence of a suppression effect of the treatment on the immune-related disease is evaluated based on the following "evaluation criteria for having an effect" and "evaluation criteria of no effect". The items C-1 and C-2 of "evaluation criteria for having an effect" can be used alone or in combination. The items D-1 and D-2 of the "evaluation criteria of no effect" can be used alone or in combination.

<Evaluation Criteria for Having an Effect>
- C-1: the number of immune-related cells each having a primary cilium in the subject specimen after treatment being significantly larger than the number of immune-related cells each having a primary cilium in the untreated specimen
- C-2: the formation rate of a primary cilium of the immune-related cell in the subject specimen after treatment being significantly higher than the formation rate of a primary cilium of the immune-related cell in the untreated specimen <Evaluation Criteria for No Effect>
- D-1: the number of immune-related cells each having a primary cilium in the subject specimen after treatment being the same as the number of immune-related cells each having a primary cilium in the untreated specimen, or being significantly smaller than the number of immune-related cells each having a primary cilium in the untreated specimen
- D-2: the formation rate of a primary cilium of the immune-related cell in the subject specimen after treatment being the same as the formation rate of a primary cilium of an immune-related cell in the untreated specimen, or being significantly lower than the formation rate of a primary cilium of the immune-related cell in the untreated specimen Change in the primary cilium of the immune-related cell in the subject specimen between before and after administration of the immune-related disease inhibitor is used as an index of a suppression effect of the immune-related disease inhibitor on the immune-related disease.

When the immune-related disease is the immune-related disease A, the presence or absence of a suppression effect of the immune-related disease inhibitor on the immune-related disease is evaluated based on the following "evaluation criteria for having an effect" and "evaluation criteria for no effect". The items a-1 to a-3 of "evaluation criteria for having an effect" can be used alone or in combination. The items b-1 to b-3 of "evaluation criteria for no effect" can be used alone or in combination.

<Evaluation Criteria for Having an Effect>
- a-1: the number of immune-related cells each having a primary cilium in the post-administration specimen being significantly smaller than the number of immune-related cells each having a primary cilium in the unadministered specimen
- a-2: the formation rate of a primary cilium of the immune-related cell in the post-administration specimen being significantly lower than the formation rate of a primary cilium of the immune-related cell in the unadministered specimen
- a-3: the length of the primary cilium of the immune-related cell in the post-administration specimen being significantly shorter than the length of the primary cilium of the immune-related cell in the unadministered specimen <Evaluation Criteria for No Effect>
- b-1: the number of immune-related cells each having a primary cilium in the post-administration specimen being the same as the number of immune-related cells each having a primary cilium in the unadministered specimen, or being significantly larger than the number of immune-related cells each having a primary cilium in the unadministered specimen
- b-2: the formation rate of a primary cilium of the immune-related cell in the post-administration specimen being the same as the formation rate of a primary cilium of the immune-related cell in the unadministered specimen, or being significantly higher than the formation rate of a primary cilium of the immune-related cell in the unadministered specimen
- b-3: the length of the primary cilium of the immune-related cell in the post-administration specimen being the same as the length of the primary cilium of the immune-related cell in the unadministered specimen, or being significantly longer than the length of the primary cilium of the immune-related cell in the unadministered specimen When the immune-related disease is the immune-related disease B, the presence or absence of a suppression effect of the immune-related disease inhibitor on the immune-related disease is evaluated based on the following "evaluation criteria for having an effect" and the following "evaluation criteria for no effect". The items c-1 and c-2 of "evaluation criteria for having an effect" can be used alone or in combination. The items d-1 and d-2 of the "evaluation criteria for no effect" can be used alone or in combination.

<Evaluation Criteria for No Effect>
- c-1: the number of immune-related cells each having a primary cilium in the post-administration specimen being significantly larger than the number of immune-related cells each having a primary cilium in the unadministered specimen
- c-2: the formation rate of a primary cilium of the immune-related cell in the post-administration specimen being significantly higher than the formation rate of a primary cilium of the immune-related cell in the unadministered specimen <Evaluation Criteria for No Effect>
- d-1: the number of immune-related cells each having a primary cilium in the post-administration specimen being the same as the number of immune-related cells each having a primary cilium in the unadministered specimen, or being significantly smaller than the number of immune-related cells each having a primary cilium in the unadministered specimen
- d-2: the formation rate of a primary cilium of the immune-related cell in the post-administration specimen being the same as the formation rate of a primary cilium of the immune-related cell in the unadministered specimen, or being significantly lower than the formation rate of a primary cilium of the immune-related cell in the unadministered specimen As described above, according to the method for evaluating a suppression effect on an immune-related disease of the present invention, the suppression effect on the immune-related disease in the subject subjected to the treatment for the immune-related disease or the subject administered with the immune-related disease inhibitor can be evaluated rapidly and objectively, since change in the primary cilium of the immune-related cell in the subject specimen between before and after the treatment or between before and after the administration of the immune-related disease inhibitor is used as an index of the suppression effect on the immune-related disease. Accordingly, the method for evaluating a suppression effect on an immune-related disease of the present invention is expected to be used for preparation of a treatment plan of an immune-related disease by a doctor, development of a treatment method of an immune-related disease, development of a therapeutic agent for an immune-related disease, and development of a quasi-drug or a cosmetic component for suppressing an immune-related disease.

5. Method for Evaluating Test Sample

The method for evaluating a test sample of the present invention is a method for evaluating a test sample, which is used for evaluating whether or not a test sample is a substance having an immune function-controlling action, and which is characterized in that the method includes the steps of:
- (A) observing a primary cilium of an immune-related cell in a cell group containing an immune-related cell having a primary cilium,
- (B) contacting the cell group containing an immune-related cell having a primary cilium with a test sample, and observing the primary cilium of the immune-related cell in the cell group contacted with the test sample, and
- (C) evaluating whether or not the test sample is a substance having an immune function-controlling action on the basis of the difference between the observations of the primary cilium of the immune-related cell in the cell group observed in the step (A) and the observations of the primary cilium of the immune-related cell in the cell group observed in the step (B).

According to the method for evaluating a test sample of the present invention, whether or not the test sample has an immune function-controlling action can be objectively and accurately evaluated by simple operations, since a procedure including the step of evaluating whether or not the test sample is a substance having an immune-function controlling action on the basis of the difference between the observations of the primary cilium of the immune-related cell in the cell group observed in the step (A) and the observation result of the primary cilium of the immune-related cell in the cell group observed in the step (B) is adopted. The "immune function-controlling action" encompasses an immune function-promoting action to increase the immune function and an immune function-suppressing action to reduce the immune function.

The order in which steps (A) and (B) are performed is arbitrary. The order can be the order of performing step (B) after performing step (A), or can be the order of performing step (A) after performing step (B). In addition, steps (A) and (B) can be performed at the same time.

The test sample is a sample to be evaluated as to whether or not the test sample has an immune function-controlling action. The test sample includes, for example, a substance expected to have an immune function-promoting action, a substance expected to have an immune function-suppressing action, or the like, and the present invention is not limited to those exemplified ones. Concrete examples of the test sample include an inorganic compound, an organic compound, a plant extract, a microorganism extract, a culture supernatant, or the like, and the present invention is not limited to those exemplified ones. The test sample can be used as it is, or can be dissolved in a solvent and used. The solvent for dissolving the test sample includes, for example, saline, phosphate-buffered saline, water, or the like, and the present invention is not limited to those exemplified ones.

In the step (A), a primary cilium of an immune-related cell in the cell group containing an immune-related cell having a primary cilium is observed. The primary cilium of the immune-related cell in the cell group can be observed after culturing the cell group containing an immune-related cell having a primary cilium in a medium in the absence of a test sample.

An immune-related cell having a primary cilium is the same as the immune-related cell used in the method for detecting an index of an immune-related disease. The immune-related cell cannot be absolutely determined, because the immune-related cell used in the method for evaluating a test sample of the present invention varies depending on the use application of the method for evaluating the test sample of the present invention and the like. It is therefore preferred to determine the immune-related cell in accordance with the use application of the method for evaluating the test sample of the present invention and the like.

The medium and culture conditions cannot be absolutely determined, because the medium and the culture conditions used for culturing the immune-related cell having a primary cilium vary depending on the kind of the immune-related cell having a primary cilium and the like. It is therefore preferred to determine the medium and culture conditions in accordance with the kind of the immune-related cell having a primary cilium and the like.

The primary cilium of the immune-related cell in the cell group can be observed in the same manner as in the observation of the primary cilium of the immune-related cells in the subject specimen in the method for detecting an index of an immune-related disease. In addition, the observation item is the same as the observation item in the method for detecting an index of an immune-related disease.

In the step (B), the cell group containing an immune-related cell having a primary cilium is contacted with the test sample, and the primary cilium of the immune-related cell in the cell group contacted with the test sample is observed. The contact between the cell group and the test sample can be performed by, for example, culturing the immune-related cell having a primary cilium in a medium in the presence of the test sample, and the like.

The immune-related cell having a primary cilium used in the step (B) is an immune-related cell having primary cilium, which is obtained from a skin tissue of the same source as that of an immune-related cell having a primary cilium used in the step (A), and which is the same kind as that of an immune-related cell having a primary cilium used in the step (A). When the step (B) is performed after performing the step (A), the immune-related cell having a primary cilium used in the step (B) can be an immune-related cell having a primary cilium used in the step (A), or can be another cell.

The medium used in the step (B) is the same kind of medium as that of the medium used in the step (A). The culture conditions of an immune-related cell having a primary cilium in the presence of the test sample is the same as the culture conditions of the immune-related cell having a primary cilium in the step (A), except that, for example, a medium containing a test sample obtained by adding a test sample to the same kind of medium as that of the medium used in the step (A) is used. The concentration of the test sample cannot be absolutely determined, because the concentration of the test sample in the medium containing the test sample varies depending on the kind of the immune-related cell having a primary cilium, the use application of the method for evaluating the test sample of the present invention, and the like. It is therefore preferred to determine the concentration of the test sample in accordance with the kind of the immune-related cell having a primary cilium, the use application of the method for evaluating the test sample of the present invention, and the like.

In the step (C), it is evaluated whether or not the test sample is a substance having an immune function-controlling action on the basis of the difference between the observations of the primary cilium of the immune-related cell in the cell group observed in the step (A) and the observations of the primary cilium of the immune-related cells in the cell group observed in the step (B).

The difference between the observations measured in the step (A) and the observations measured in the step (B) includes a difference in the number of immune-related cells each having a primary cilium in the cell group depending on the presence or absence of the test sample, a difference in the formation rate of a primary cilium of the immune-related cell in the cell group depending on the presence or absence of the test sample, a difference in the length of a primary cilium of the immune-related cell in the cell group depending on the presence or absence of the test sample, or the like, and the present invention is not limited to those exemplified ones. The difference between the observations measured in the step (A) and the observations measured in the step (B) can be examined in the same manner as in the comparison of the observations of the primary cilium of the immune-related cell between the subject specimen and the normal specimen in the method for detecting an index of an immune-related disease.

The index showing that the test sample has an immune function-controlling action include, for example, the following indices a to d, or the like, and the present invention is not limited to those exemplified ones. These indices can be used alone or in combination.

<Index a>

There is a significant difference between the number of immune-related cells each having a primary cilium in the cell group measured in the step (B) and the number of immune-related cells each having a primary cilium in the cell group measured in the step (A).

<Index b>

There is a significant difference between the formation rate of a primary cilium of the immune-related cell calculated from the number of immune-related cells each having a primary cilium in the cell group measured in the step (B) and the formation rate of a primary cilium of the immune-related cell calculated from the number of immune-related cells each having a primary cilium in the cell group measured in the step (A).

<Index c>

There is a significant difference between the number of primary cilia per immune-related cell in the cell group measured in the step (B) and the number of primary cilia per immune-related cell in the cell group measured in the step (A).

<Index d>

There is a significant difference between the length of the primary cilium of the immune-related cell in the cell group measured in the step (B) and the length of the primary cilium of the immune-related cell in the cell group measured in the step (A).

When the immune-related cell is a peripheral blood mononuclear cell or a dendritic cell, it is evaluated that the test sample exhibits an immune function-suppressing action at the affected part of the immune-related disease A based on the following indices a-1 to c-1.

<Index a-1>

The number of immune-related cells each having a primary cilium in the cell group measured in the step (B) being significantly smaller than the number of immune-related cells each having a primary cilium in the cell group measured in the step (A)

<Index b-1>

The formation rate of a primary cilium of the immune-related cell calculated from the number of immune-related cells each having a primary cilium in the cell group measured in the step (B) being significantly lower than the formation rate of a primary cilium of the immune-related cell calculated from the number of immune-related cells each having a primary cilium in the cell group measured in the step (A)

<Index c-1>

The length of the primary cilium of the immune-related cell in the cell group measured in the step (B) being significantly shorter than the length of the primary cilium of the immune-related cell in the cell group measured in the step (A)

When the immune-related cell is a fibroblast or an epithelial cell derived from the tissue of the immune-related disease B, it is evaluated that the test sample exhibits an immune function-suppressing action at the affected part of the immune-related disease B based on the following indices a-2 and b-2.

<Index a-2>

The number of immune-related cells each having a primary cilium in the cell group measured in the step (B) being significantly larger than the number of immune-related cells each having a primary cilium in the cell group measured in the step (A)

<Index b-2>

The formation rate of the primary cilium of the immune-related cell calculated from the number of immune-related cells each having a primary cilium in the cell group measured in the step (B) being significantly higher than the formation rate of a primary cilium of the immune-related cell calculated from the number of immune-related cells each having a primary cilium in the cell group measured in the step (A)

As described above, according to the method for evaluating a test sample of the present invention, whether or not the test sample has an immune function-controlling action by simple operations can be evaluated objectively and accurately. Accordingly, the method for evaluating a test sample of the present invention is expected to be used for screening of an immune function-controlling substance, evaluation of effectiveness of an immune function-controlling substance, development of a therapeutic agent for an immune-related disease, development of a quasi-drug or a cosmetic component for suppressing an immune-related disease, and the like.

6. Immune Function-Controlling Agent

The immune function-controlling agent of the present invention is an immune function-controlling agent for suppressing an immune function, which is characterized in that the immune function-controlling agent includes as an active ingredient an active substance having an action of removing a primary cilium, which has an action of removing a primary cilium from an immune-related cell having a primary cilium.

According to the immune function-controlling agent of the present invention, the immune function can be effectively controlled, since the immune function-controlling agent includes as an active ingredient the substance having an action of removing a primary cilium. The concept of "immune function-controlling agent" encompasses an immune function inhibitor having an immune function-suppressing action and an immune function promoter having an immune function-promoting action.

The primary cilium-removing substance can be obtained by performing the steps (A) and (B) in the method for evaluating a test sample, in which the observations of the primary cilium of the immune-related cell in the cell group observed in the step (B) being smaller than the observations of the primary cilium of the immune-related cells in the cell group observed in the step (A) is used as an index. The substance having an action of removing a primary cilium includes, for example, a steroid, a physiologically active substance, or the like, and the present invention is not limited to those exemplified ones.

The steroid includes, for example, cortisone-based steroids such as cortisone or cortisone acetate; a hydrocortisone-based steroid such as hydrocortisone, hydrocortisone sodium phosphate, hydrocortisone sodium succinate, hydrocortisone acetate, hydrocortisone butyrate, or hydrocortisone butyrate propionate; a dexamethasone-based steroid such as dexamethasone, dexamethasone propionate, dexamethasone valerate, dexamethasone acetate, dexamethasone sodium phosphate, or dexamethasone palmitate; a betamethasone-based steroid such as betamethasone, betamethasone dipropionate, betamethasone butyrate propionate, or betamethasone valerate; prednisolone-based steroids such as prednisolone, prednisolone acetate, prednisolone sodium succinate, prednisolone butylacetate, or prednisolone sodium phosphate; a methylprednisolone-based steroid such as methylprednisolone, methylprednisolone acetate, or methylprednisolone sodium succinate; a triamcinolone-based steroid such as triamcinolone, triamcinolone diacetate, or triamcinolone acetonide; or the like, and the present invention is not limited to those exemplified ones. The physiologically active substance includes, for example, tumor necrosis factor alpha (TNFα), prostaglandin E2, or the like, and the present invention is not limited to those exemplified ones.

The substance having an action of removing a primary cilium can form a solvate. The solvate includes, for example, a hydrate, an ethanolate, a dimethyl sulfoxide adduct, or the like, and the present invention is not limited to those exemplified ones.

The content cannot be absolutely determined, because the content of the substance having an action of removing a primary cilium in the immune function-controlling agent of the present invention varies depending on the use application of the immune function-controlling agent of the present invention, the kind of the substance, and the like. It is therefore preferred to determine the content in accordance with the use application of the immune function-controlling agent of the present invention, the kind of the substance, and the like. The content of the substance having an action of removing a primary cilium in the immune function-controlling agent of the present invention is preferably 5% by mass or less, and more preferably 1% by mass or less, from the viewpoint of reducing the load on the normal cell. The lower limit of the content of the substance having an action of removing a primary cilium in the immune function-controlling agent of the present invention can be within a range that an action of removing a primary cilium from an immune-related cell having a primary cilium is exhibited. The lower limit of the content of the substance having an action of removing a primary cilium in the immune function-controlling agent of the present invention is usually preferably 0.000001% by mass or more, and more preferably 0.0001% by mass or more.

The immune function-controlling agent of the present invention can include a binder, a stabilizer, an excipient, a solubilizing agent, an isotonizing agent, a buffer solution, and the like within a scope which would not hinder an object of the present invention.

The immune function-controlling agent of the present invention can be used as an immune function inhibitor having an immune function-suppressing action on a subject affected with an immune-related disease caused by expression of an excessive immune function due to an abnormal increase in primary cilia. The immune-related disease caused by expression of an excessive immune function due to an abnormal increase of primary cilia includes, for example, hyper-IgE syndrome, chronic granulomatosis, arthritis, autoimmune hepatitis, autoimmune glomerulonephritis, autoimmune pancreatitis, autoimmune testitis, autoimmune ovaritis, ulcerative colitis, Sjogren's syndrome, Crohn's disease, Bechet's disease, Wegener's granulomatosis, hypersensitivity vasculitis, periarteritis nodosa, Hashimoto's disease, myxedema, Basedow's disease, Addison's disease, autoimmune hemolytic anemia, sudden thrombocytopenia, pernicious anemia, myasthenia gravis, demyelinating disease, aortitis syndrome, psoriasis, pemphigus, pemphigoid, collagenosis (for example, systemic lupus erythematosus, chronic rheumatoid arthritis, diffuse scleroderma, systemic progressive sclerosis, dermatomyositis, polyarteritis nodosa, rheumatic fever, or the like), Guillain-Barre syndrome, polyglandular autoimmune syndrome type II, primary biliary cirrhosis, vitiligo, type 1 diabetes, autoimmune thrombosis (for example, autoimmune arterial thrombosis, autoimmune venous thrombosis, or the like), habitual abortion, thrombocytopenia, antiphospholipid antibody syndrome, or the like, and the present invention is not limited only to those exemplified ones.

As described above, according to the immune function-controlling agent of the present invention, the immune function can be effectively controlled, since the immune function-controlling agent of the present invention includes as an active ingredient the substance having an action of removing a primary cilium. Accordingly, the immune function-controlling agent of the present invention is expected to be suitably used for a therapeutic agent for an immune-related disease, a quasi-drug or a cosmetic ingredient for suppressing an immune-related disease. When the immune function-controlling agent of the present invention is an immune function promoter, the immune function-controlling agent is expected to be suitably used for a therapeutic agent for an immune-related disease caused by deterioration of an immune function due to an abnormal increase in primary cilia, a quasi-drug or a cosmetic component for suppressing the immune-related disease, or the like. When the immune function-controlling agent of the present invention is an immune function inhibitor, the immune function-controlling agent is expected to be suitably used as a therapeutic agent for an immune-related disease caused by expression of an excessive immune function due to an abnormal increase of primary cilia, and a quasi-drug or a cosmetic ingredient for suppressing the immune-related disease, or the like.

7. Agent for Removing Primary Cilium of Immune-Related Cell

The agent for removing a primary cilium of an immune-related cell of the present invention is an agent for removing a primary cilium of an immune-related cell, which is used for removing a primary cilium from an immune-related cell having a primary cilium, and which is characterized in that the agent includes as an active ingredient at least one kind selected from the group consisting of a steroid and a physiologically active substance.

According to the agent for removing a primary cilium of an immune-related cell of the present invention, a primary cilium of an immune-related cell can be removed, since the agent for removing a primary cilium of an immune-related cell of the present invention includes at least one kind selected from the group consisting of a steroid and a physiologically active substance as an active ingredient.

The steroid and the physiologically active substance used in the agent for removing a primary cilium of an immune-related cell of the present invention are the same as the steroid and the physiologically active substance used as the active ingredient of the immune function-controlling agent.

The content cannot be absolutely determined, because the content of the active ingredient in the agent for removing a primary cilium of an immune-related cell of the present invention varies depending on the use application of the agent for removing a primary cilium of an immune-related cell of the present invention, the kind of the active ingredient, and the like. It is therefore preferred to determine the content in accordance with the use application of the agent for removing a primary cilium of an immune-related cell of the present invention, the kind of the active ingredient, and the like. The content of the active ingredient in the agent for removing a primary cilium of an immune-related cell of the present invention is preferably 5% by mass or less, and more preferably 1% by mass or less from the viewpoint of reducing the load on the normal cell.

As described above, since the agent for removing a primary cilium of an immune-related cell of the present invention can remove a primary cilium of an immune-related cell, the agent for removing a primary cilium of an immune-related cell of the present invention is expected to be suitably used for a quasi-drug or a cosmetic component for suppressing an immune-related disease caused by abnormality in function of a primary cilium of an immune-related cell.

EXAMPLES

The present invention will be explained in more detail by means of Examples below, but the present invention is not limited only to such Examples. Meaning of each abbreviation used below is as follows:

Explanation of Abbreviations

DMSO: dimethyl sulfoxide
EDTA: ethylenediaminetetraacetic acid
FBS: fetal bovine serum
PBS: phosphate-buffered saline
PFA: paraformaldehyde
TNF: tumor necrosis factor
IL-4: interleukin-4
GM-CSF: granulocyte macrophage colony stimulating factor Example 1

A skin piece was obtained from a human healthy skin tissue (obtained from national university corporation, Graduate School of Medicine, Osaka University). The obtained skin piece was embedded in an embedding agent for preparing a frozen tissue section (manufactured by Sakura Finetek Japan Co., Ltd., trade name: Tissue-Tek O.C.T. Compound). The embedded skin piece was frozen in isopentane cooled with liquid nitrogen, to give a frozen skin piece. Next, the frozen skin piece was cut with a cryomicrotome, to give a section (thickness: 10 μm). The obtained section was fixed by immersing in 4 v/v % PFA-containing PBS solution at a room temperature for 10 minutes. The fixed section was blocked and permeabilized in a blocking/permeabilization agent [0.1 v/v % polyethylene glycol tert-octylphenyl ether (Triton X-100) and 10 v/v % FBS-containing PBS solution], to give a sample.

The obtained sample was reacted with an anti-tubulin antibody (manufactured by Sigma-Aldrich, trade name: MONOCLONAL ANTI-ACETYLATED TUBULIN CLONE 6-11B-1, product number: T6793) and an anti-langerin antibody (manufactured by Abcam, trade name: Anti-Langerin [EPR15863] antibody, catalog number: ab192027) at 4° C. for 16 hours. The resulting reacted sample was washed with a washing solution (0.1 w/w % polyoxyethylene sorbitan monolaurate (Tween-20)-containing PBS solution).

The anti-langerin antibody is an antibody against a Langerhans cell marker, and the anti-tubulin antibody is an antibody against a primary cilium marker.

The washed sample was stained by reacting the sample with a fluorescent dye-labeled anti-mouse IgG antibody [manufactured by Abcam, trade name: Goat Anti-Mouse IgG H&L (fluorescent dye: Alexa Fluor (registered trademark) 594, catalog number: ab150116], a fluorescent dye-labeled anti-rabbit IgG antibody [manufactured by Abcam, trade name: Goat Anti-Rabbit IgG H&L (fluorescent dye: Alexa Fluor (registered trademark) 488), catalog number: ab150077], and a cell nucleus-staining agent [2'-(4-ethoxyphenyl)-5-(4-methyl-1-piperazinyl)-2,5'-bi-1H-benzimidazole trihydrochloride (Hoechst33342)] at a room temperature (25° C.) for 3 hours. The stained sample was washed with a washing solution A.

The washed sample was mounted in an antifade mountant [manufactured by Thermo Fisher Scientific K.K., trade name: ProLong (registered trademark) Gold antifade mountant, product number: P36934], to give an observation sample. Using the obtained observation sample and a confocal microscope (manufactured by Olympus Corporation, product number: FV1200), the sample was observed by detecting a Langerhans cell marker, a primary cilium marker and a cell nucleus-staining agent contained in the observation sample.

Figure 1B:
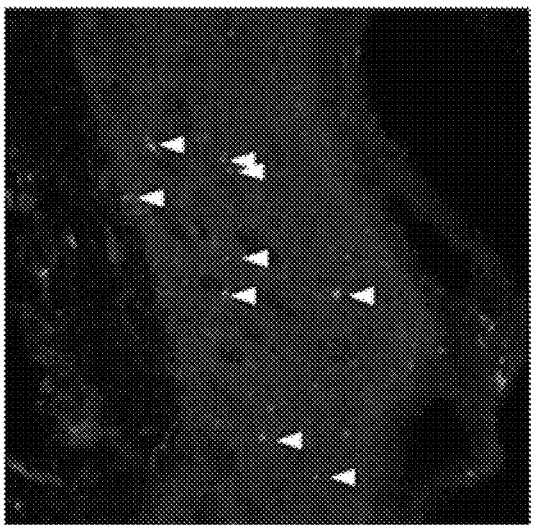
FIG. 1(B) is a photograph substituted for a drawing, showing a stained image of a human healthy skin tissue based on a primary cilium marker.
Figure 1C:
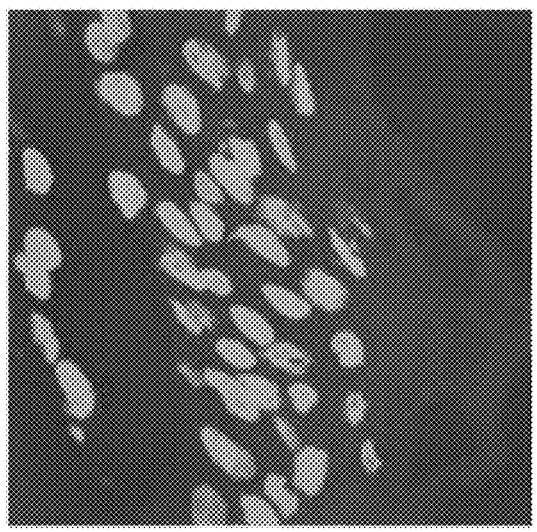
FIG. 1(C) is a photograph substituted for a drawing, showing a stained image of a human healthy skin tissue based on a cell nucleus-staining agent.
Figure 1D:
FIG. 1(D) is a photograph substituted for a drawing, showing a superposed image of the stained image shown in FIG. 1(A), the stained image shown in FIG. 1(B), and the stained image shown in FIG. 1(C).

In Example 1, a stained image of a human healthy skin tissue based on a Langerhans cell marker is shown in FIG. 1(A); a stained image of a human healthy skin tissue based on a primary cilium marker is shown in FIG. 1(B); a stained image of a human healthy skin tissue based on a cell nucleus-staining agent is shown in FIG. 1(C); and a superposed image of the stained image shown in FIG. 1(A), the stained image shown in FIG. 1(B), and the stained image shown in FIG. 1(C) is shown in FIG. 1(D). In the figures, the scale bar indicates 10 μm.

From the results shown in FIGS. 1(A) to 1(D), it can be seen that a primary cilium marker is detected in a portion where a Langerhans cell marker in the skin tissue is stained. Accordingly, it can be seen that a healthy Langerhans cell contained in a human healthy skin tissue has a primary cilium.

Example 2

A fixed and paraffin-embedded atopic dermatitis skin tissue [manufactured by Asterand Bioscience, Patient ID: 95253] was cut with a microtome for paraffin, to obtain a section (thickness: 7 μm).

The obtained section was deparaffinized by immersing the obtained section in xylene for 5 minutes. The deparaffinized section was hydrated in a stepwise manner by washing the deparaffinized section using ethanol, 95% by volume aqueous ethanol solution and purified water in this order. The hydrated section was boiled in 1 mM aqueous EDTA solution for 15 minutes, to activate an antigen. The obtained section was blocked and permeabilized by incubating the section in a blocking/permeabilizing agent, to obtain a sample.

The obtained sample was reacted with an anti-tubulin antibody [manufactured by Sigma-Aldrich, trade name: MONOCLONAL ANTI-ACETYLATED TUBULIN CLONE 6-11B-1, product number: T6793] and an anti-langerin antibody [manufactured by Abcam, trade name: Anti-Langerin [EPR15863] antibody, catalog number: ab192027] at 4° C. for 16 hours. The reacted sample was washed with a washing solution A [0.1 w/w % polyoxyethylene sorbitan monolaurate (Tween-20)-containing PBS solution].

The washed sample was stained with a fluorescent dye-labeled anti-mouse IgG antibody [manufactured by Abcam, trade name: Goat Anti-Mouse IgG H&L (fluorescent dye: Alexa Fluor (registered trademark) 488, catalog number: ab150113] and a fluorescent dye-labeled anti-rabbit IgG antibody [manufactured by Abcam, trade name: Goat Anti-Rabbit IgG H&L (fluorescent dye: Alexa Fluor (registered trademark) 594), catalog number: ab150080] at a room temperature (25° C.) for 3 hours. The stained sample was washed with a washing solution A.

The washed sample was mounted in an antifade mountant [manufactured by Thermo Fisher Scientific K.K., trade name: ProLong (registered trademark) Gold antifade mountant, product number: P36934], to give an observation sample. Using the obtained observation sample and a confocal microscope (manufactured by Olympus Corporation, product number: FV1200), the sample was observed by detecting a Langerhans cell marker, a primary cilium marker and a cell nucleus-staining agent contained in the observation sample.

Figure 2A:
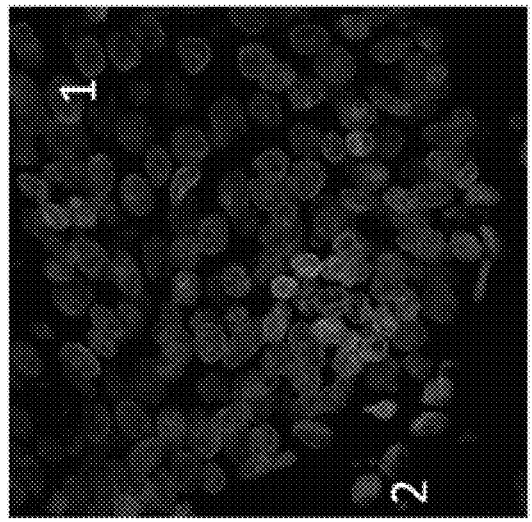
FIG. 2(A) is a photograph substituted for a drawing, showing a stained image of an atopic dermatitis lesion tissue based on a primary cilium marker, examined in Example 2.
Figure 2C:
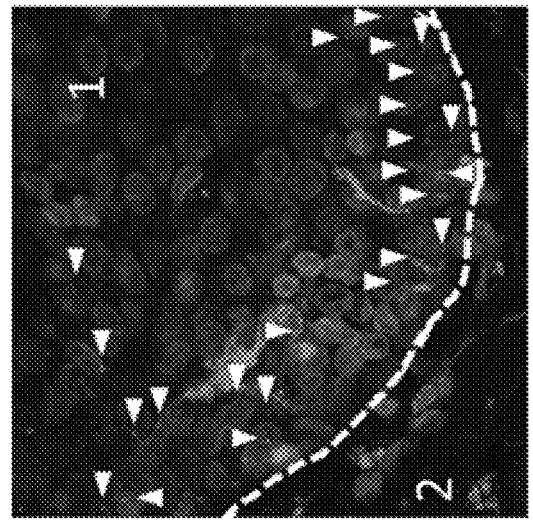
FIG. 2(C) is a photograph substituted for a drawing, showing a stained image of an atopic dermatitis lesion tissue based on a cell nucleus-staining agent.
Figure 2B:
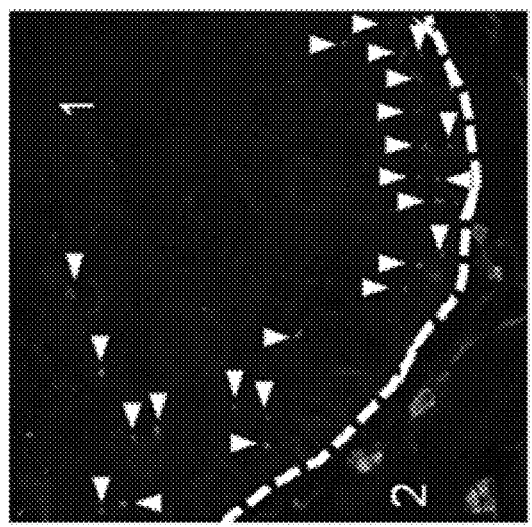
FIG. 2(B) is a photograph substituted for a drawing, showing a stained image of an atopic dermatitis lesion tissue based on a Langerhans cell marker.
Figure 2D:
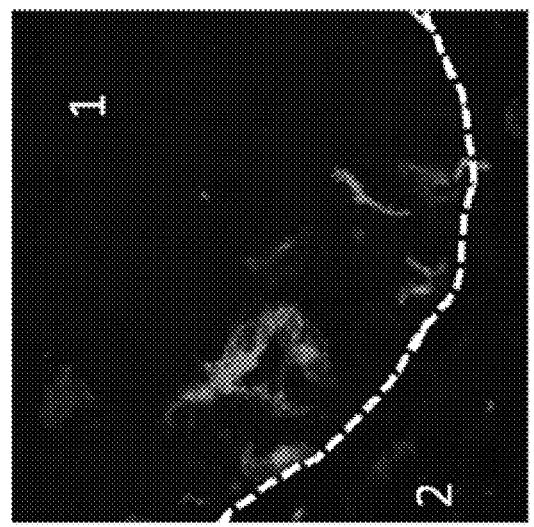
FIG. 2(D) is a photograph substituted for a drawing, showing a superposed image of the stained image shown in FIG. 2(A), the stained image shown in FIG. 2(B), and the stained image shown in FIG. 2(C).

In Example 2, a stained image of an atopic dermatitis lesion tissue based on a primary cilium marker is shown in FIG. 2(A); a stained image of an atopic dermatitis lesion tissue based on a Langerhans cell marker is shown in FIG. 2(B); a stained image of an atopic dermatitis lesion tissue based on a cell nucleus-staining agent is shown in FIG. 2(C); and a superposed image of the stained image shown in FIG. 2(A), the stained image shown in FIG. 2(B), and the stained image shown in FIG. 2(C) is shown in FIG. 2(D). In the figures, 1 denotes an epidermis; 2 denotes a dermis; a white arrow indicates a primary cilium marker; and the scale bar indicates 20 µm.

Figure 3C:
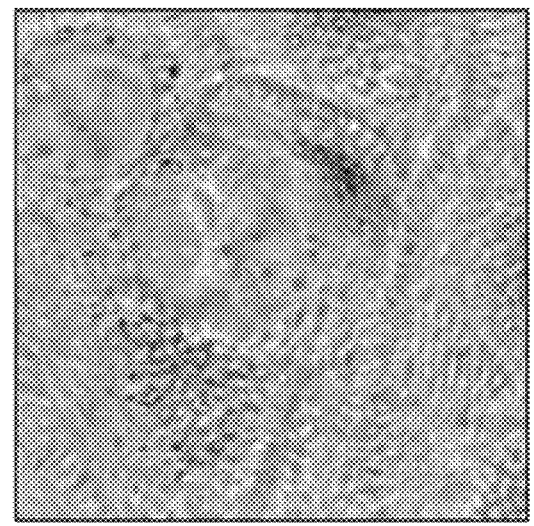
FIG. 3(C) is a photograph substituted for a drawing, showing a photographed image of an atopic dermatitis lesion tissue photographed in accordance with a differential interference observation method.
Figure 3D:
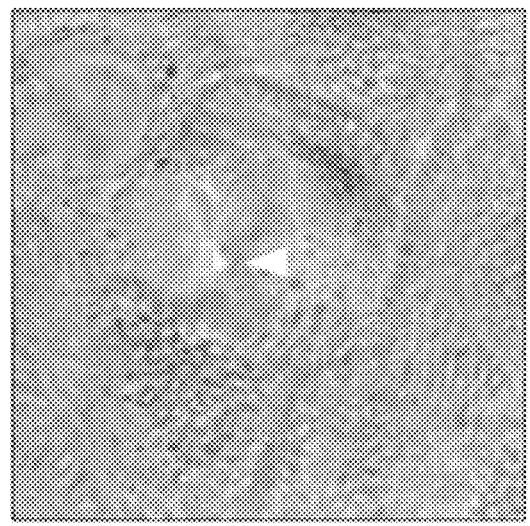
FIG. 3(D) is a photograph substituted for a drawing, showing a superposed image of the stained image shown in FIG. 3(A), the stained image shown in FIG. 3(B), and the photographed image shown in FIG. 3(C).
Figure 3A:
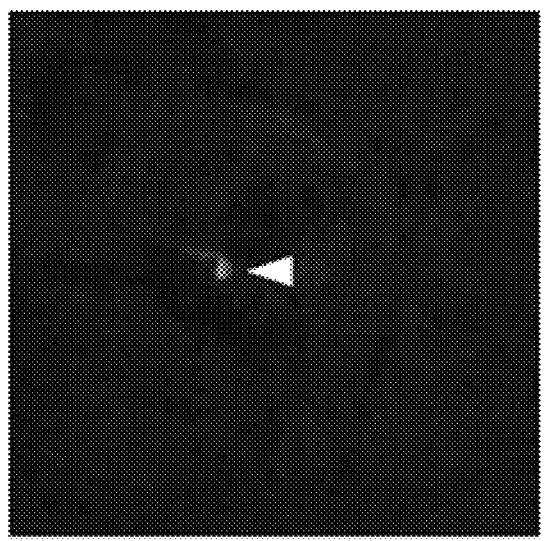
FIG. 3(A) is a photograph substituted for a drawing, showing a stained image of a Langerhans cell in an atopic dermatitis lesion tissue based on a primary cilium marker, examined in Example 2.
Figure 3B:
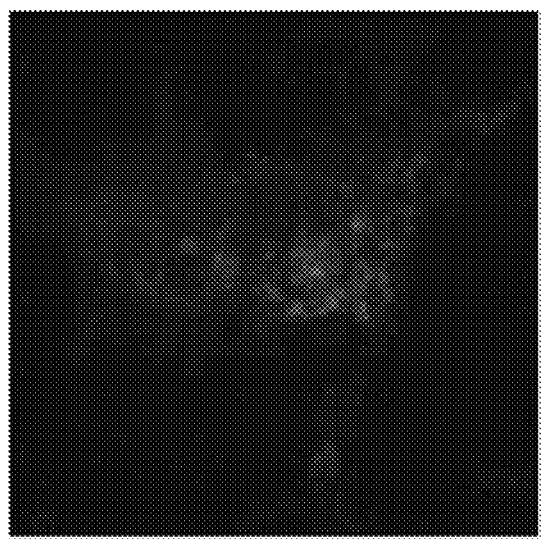
FIG. 3(B) is a photograph substituted for a drawing, showing a stained image of a Langerhans cell in an atopic dermatitis lesion tissue based on a Langerhans cell marker.

In addition, in Example 2, a stained image of a Langerhans cell in the atopic dermatitis lesion tissue based on the primary cilium marker is shown in FIG. 3(A); a stained image of a Langerhans cell in the atopic dermatitis lesion tissue based on the Langerhans cell marker is shown in FIG. 3(B); a photographed image of a Langerhans cell in the atopic dermatitis lesion tissue photographed by a differential interference observation method is shown in FIG. 3(C); and a superposed image of the stained image shown in FIG. 3(A), stained image shown in FIG. 3(B), and the photographed image shown in FIG. 3(C) is shown in FIG. 3(D). In the figures, a white arrow indicates a primary cilium marker and the scale bar indicates 5 µm.

From the results shown in FIGS. 2(A) to 2(D), it can be seen that a primary cilium marker is detected in a region where a Langerhans cell marker in an epidermis in an atopic dermatitis lesion tissue is stained. In addition, from the results shown in FIGS. 3(A) to 3(D), it can be seen that a primary cilium marker is detected in a Langerhans cell. Accordingly, from these results, it can be seen that a large number of Langerhans cells each having a primary cilium are present in the lesion tissue of atopic dermatitis.

Example 3

Using the number of Langerhans cells each having a primary cilium as an observation item, the number of Langerhans cells each having a primary cilium in the normal tissue and the number of Langerhans cells each having a primary cilium in the atopic dermatitis lesion tissue were obtained by observing the observation sample derived from the human healthy skin tissue (normal tissue) obtained in Example 1 and the observation sample derived from the atopic dermatitis lesion tissue obtained in Example 2.

Figure 4:
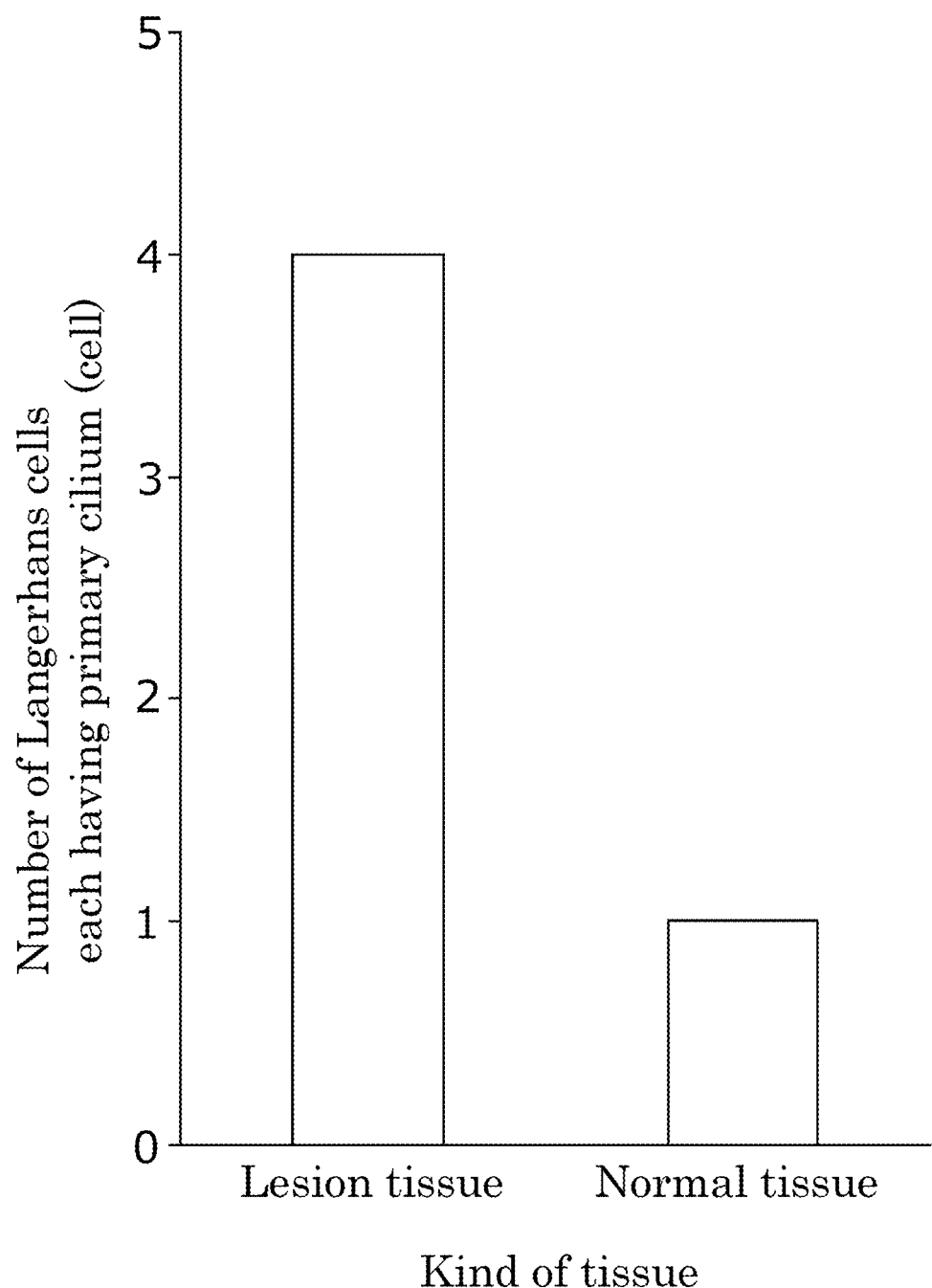
FIG. 4 is a graph showing results of examination of the relationship between the kind of the tissue and the number of Langerhans cells each having a primary cilium, examined in Example 3.

Results of examination of the relationship between the kind of tissue and the number of Langerhans cells each having a primary cilium are shown in FIG. 4. FIG. 4 is a graph showing results of examination of the relationship between the kind of tissue and the number of Langerhans cells each having a primary cilium in Example 3.

From the results shown in FIG. 4, it can be seen that the number of Langerhans cells each having a primary cilium in the atopic dermatitis lesion tissue is larger than the number of Langerhans cells each having a primary cilium in the normal tissue. Accordingly, it can be seen that the Langerhans cells each having a primary cilium are increased in the atopic dermatitis lesion tissue as compared with that in the normal tissue. Additionally, although not shown, it has been confirmed from the stained image that the primary cilium of the Langerhans cell of the atopic dermatitis lesion tissue is longer than the primary cilium of the Langerhans cell of the normal tissue.

Furthermore, using the number of keratinocytes each having a primary cilium as an observation item, the number of keratinocytes each having a primary cilium in the normal tissue and the number of keratinocytes each having a primary cilium in the atopic dermatitis lesion tissue were obtained by observing the observation sample derived from the normal tissue obtained in Example 1 and the observation sample derived from the atopic dermatitis lesion tissue obtained in Example 2. The epidermis can be distinguished from the dermis on the basis of a difference in the stained image of the cell nucleus. Ninety-five percent of cells constituting the epidermis are keratinocytes. Accordingly, it is considered that an anti-langerin antibody-nonpositive cell in the epidermis is keratinocytes. Thus, upon observation, anti-langerin antibody-nonpositive cells in the epidermis were used as keratinocytes.

Figure 5:
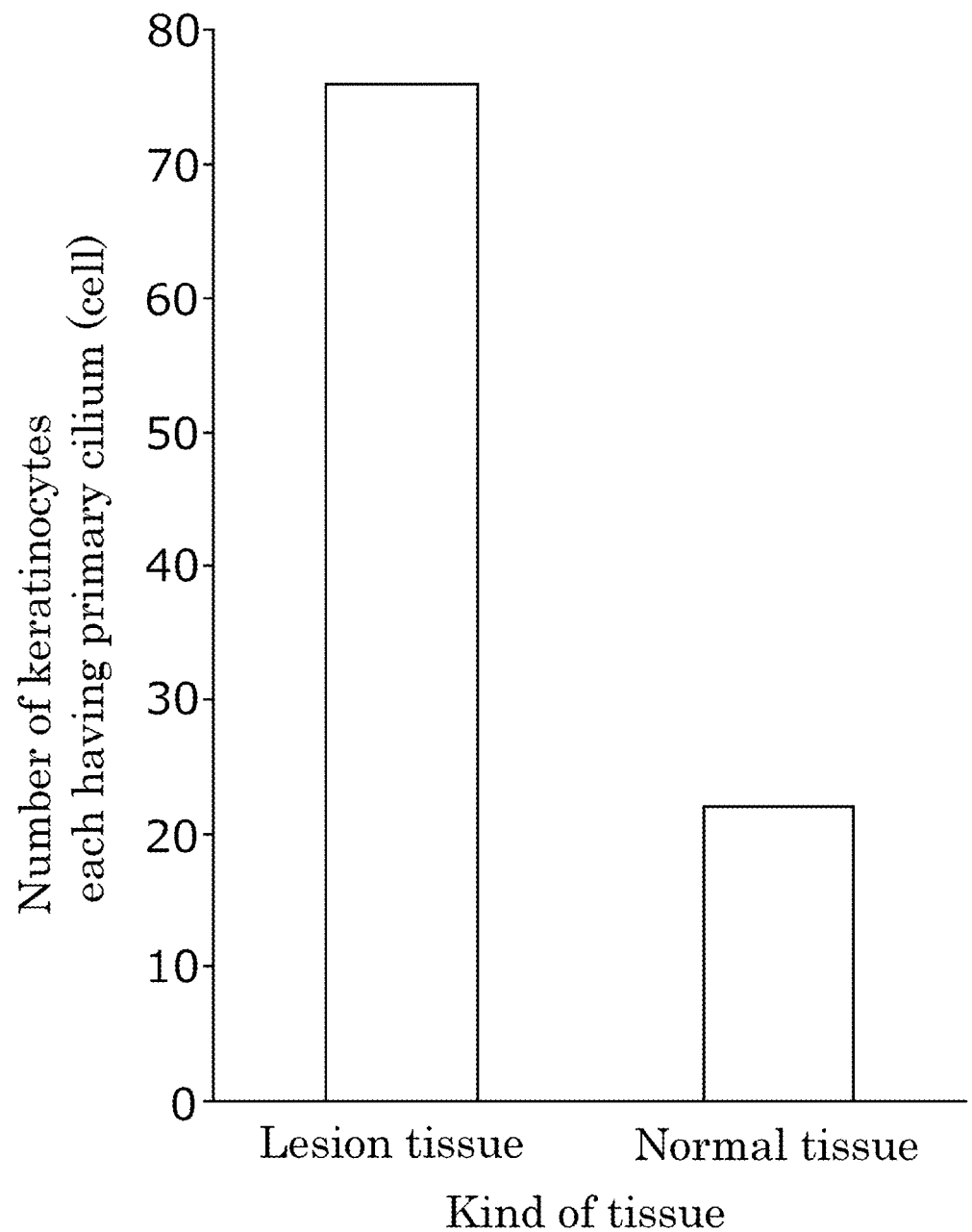
FIG. 5 is a graph showing results of examination of the relationship between the kind of the tissue and the number of keratinocytes each having a primary cilium, examined in Example 3.

Results of examination of the relationship between the kind of tissue and the number of keratinocytes each having a primary cilium are shown in FIG. 5. FIG. 5 is a graph showing results of examination of the relationship between the kind of tissue and the number of keratinocytes each having a primary cilium in Example 3.

From the results shown in FIG. 5, it can be seen that the number of keratinocytes each having a primary cilium in the atopic dermatitis lesion tissue is larger than the number of keratinocytes each having a primary cilium in the normal tissue. Accordingly, it can be seen that the keratinocytes each having a primary cilium are increased in the lesion tissue of the atopic dermatitis as compared with the normal tissue. In addition, although not shown, it has been confirmed from the stained image that the primary cilium of a keratinocyte in the atopic dermatitis lesion tissue is longer than the primary cilium of the keratinocyte in the normal tissue.

The Langerhans cell is an immune cell present in the skin. The keratinocyte is an immune function-possessing cell present in the skin. Accordingly, it can be seen that an increase in immune cells each having a primary cilium and/or cells possessing an immune function is associated with atopic dermatitis.

As explained above, it can be seen that difference between observations of a primary cilium of an immune-related cell in a subject specimen and observations of a primary cilium of an immune-related cell in a normal specimen can be detected as an index of an immune-related disease by observing the primary cilium of the immune-related cell in the subject specimen such as a lesion tissue, and comparing the observations of the primary cilium of the immune-related cell in the subject specimen with the observations of the primary cilium of the immune-related cell in the normal specimen such as a skin tissue. In addition, it can be seen that information for assisting diagnosis of the presence or absence of affection with an immune-related disease in a subject or information for assisting diagnosis of prognosis of an immune-related disease in a subject can be obtained on the basis of the obtained comparison result.

Example 4

Using 10 mL of peripheral blood collected from a healthy volunteer and 15 mL of human lymphocyte-separation medium (manufactured by GE Healthcare, trade name: Ficoll-Paque PLUS), peripheral blood mononuclear cells were separated from the peripheral blood, according to a density gradient centrifugation method. The peripheral blood mononuclear cells were cultured in a medium (RPMI 1640 medium containing 50 ng/mL IL-4, 50 ng/mL GM-CSF and 10 v/v % FBS) at 37° C. for 7 days, to differentiate the peripheral blood mononuclear cells into dendritic cells.

In order to examine change in characteristics of the cells with the passage of time, each cell after one day, three days and seven days passed from the initiation of culture was collected, and immediately fixed with 4 v/v % PFA-containing PBS solution. The fixed cells were blocked and permeabilized by incubating each fixed cell in a blocking/permeabilizing agent, to give a sample containing immature dendritic cells after one day passed from the initiation of culture, a sample containing immature dendritic cells after three days passed from the initiation of culture, and a sample containing immature dendritic cells after seven days passed from the initiation of culture.

Each of the obtained samples was reacted with an anti-tubulin antibody (manufactured by Sigma-Aldrich, trade name: MONOCLONAL ANTI-ACETYLATD TUBULIN CLONE 6-11B-1, product number: T6793) and an anti-pericentrin antibody (manufactured by Bethyl Laboratories, Inc., trade name: Pericentrin/Kendrin Antibody, product number: A301-348A-T) at a room temperature for 1 hour. Each of the reacted samples was washed with a washing solution A (0.1 w/w % polyoxyethylene sorbitan monolaurate-containing PBS solution). The anti-pericentrin antibody is an antibody against a cell nucleus marker.

Each of the washed samples was stained by reacting each sample with a fluorescent dye-labeled anti-mouse IgG antibody [manufactured by Abcam, trade name: Goat Anti-Mouse IgG H&L (fluorescent dye: Alexa Fluor (registered trademark) 488, catalog number: ab150113)] and a fluorescent dye-labeled anti-rabbit IgG antibody [manufactured by Abcam, trade name: Goat Anti-Rabbit IgG H&L (fluorescent dye: Alexa Fluor (registered trademark) 594, catalog number: ab150080)] at a room temperature (25° C.) for 3 hours. Each of the stained samples was washed with the washing solution A.

The washed sample was mounted in an antifade mountant [manufactured by Thermo Fisher Scientific K.K., trade name: ProLong (registered trademark) Gold antifade mountant, product number: P36934]. Using each of the obtained samples and a confocal microscope (manufactured by Olympus Corporation, product number: FV1200), an immature dendritic cell contained in each sample was observed by detecting a cell nucleus marker and a primary cilium marker contained in the sample.

Figure 6A:
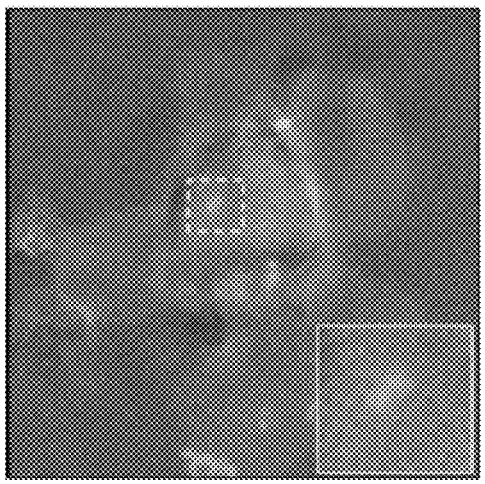
FIG. 6(A) is a photograph substituted for a drawing, showing observations of immature dendritic cells after one day passed from the initiation of the culture, examined in Example 4.
Figure 6B:
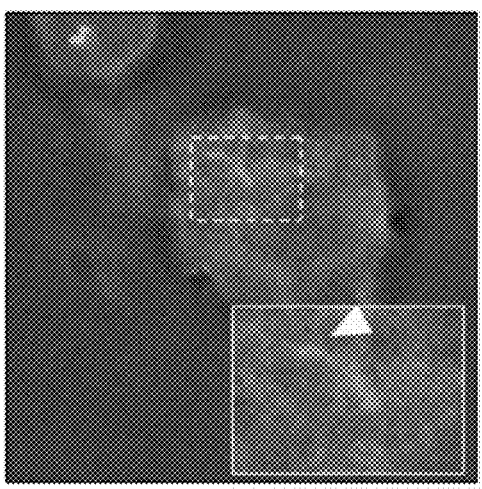
FIG. 6(B) is a photograph substituted for a drawing, showing observations of immature dendritic cells after three days passed from the initiation of the culture.
Figure 6C:
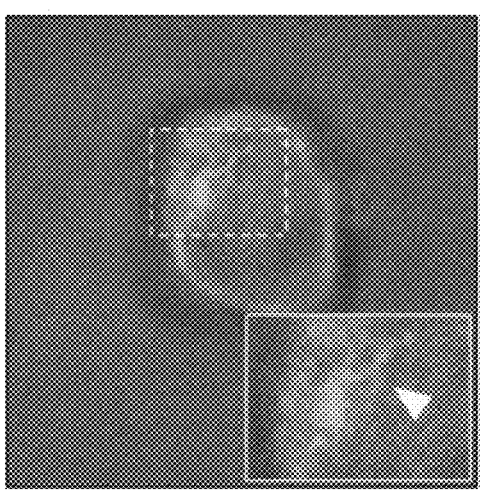
FIG. 6(C) is a photograph substituted for a drawing, showing observations of immature dendritic cells after seven days passed from the initiation of the culture.

In Example 4, observations of the immature dendritic cell after one day passed from the initiation of culture are shown in FIG. 6(A); observations of the immature dendritic cell after three days passed from the initiation of culture are shown in FIG. 6(B); and observations of the immature dendritic cell after seven days passed from the initiation of culture are shown in FIG. 6(C). In the figures, a white arrow indicates a primary cilium marker, and the scale bar indicates 5 μm. In addition, a part surrounded by a white solid line is an enlarged view of a part surrounded by a broken line.

Next, the total number of immature dendritic cells and the number of primary cilia of immature dendritic cells were obtained by using the observations of the immature dendritic cell contained in each of the samples. Then, the formation rate of the primary cilium in the immature dendritic cell was calculated in accordance with the formula (Ia):

[Formation rate of primary cilium in immature dendritic cell]=[(Number of primary cilia in immature dendritic cell)/(Total number of immature dendritic cells)]×100     (Ia).

Figure 7:
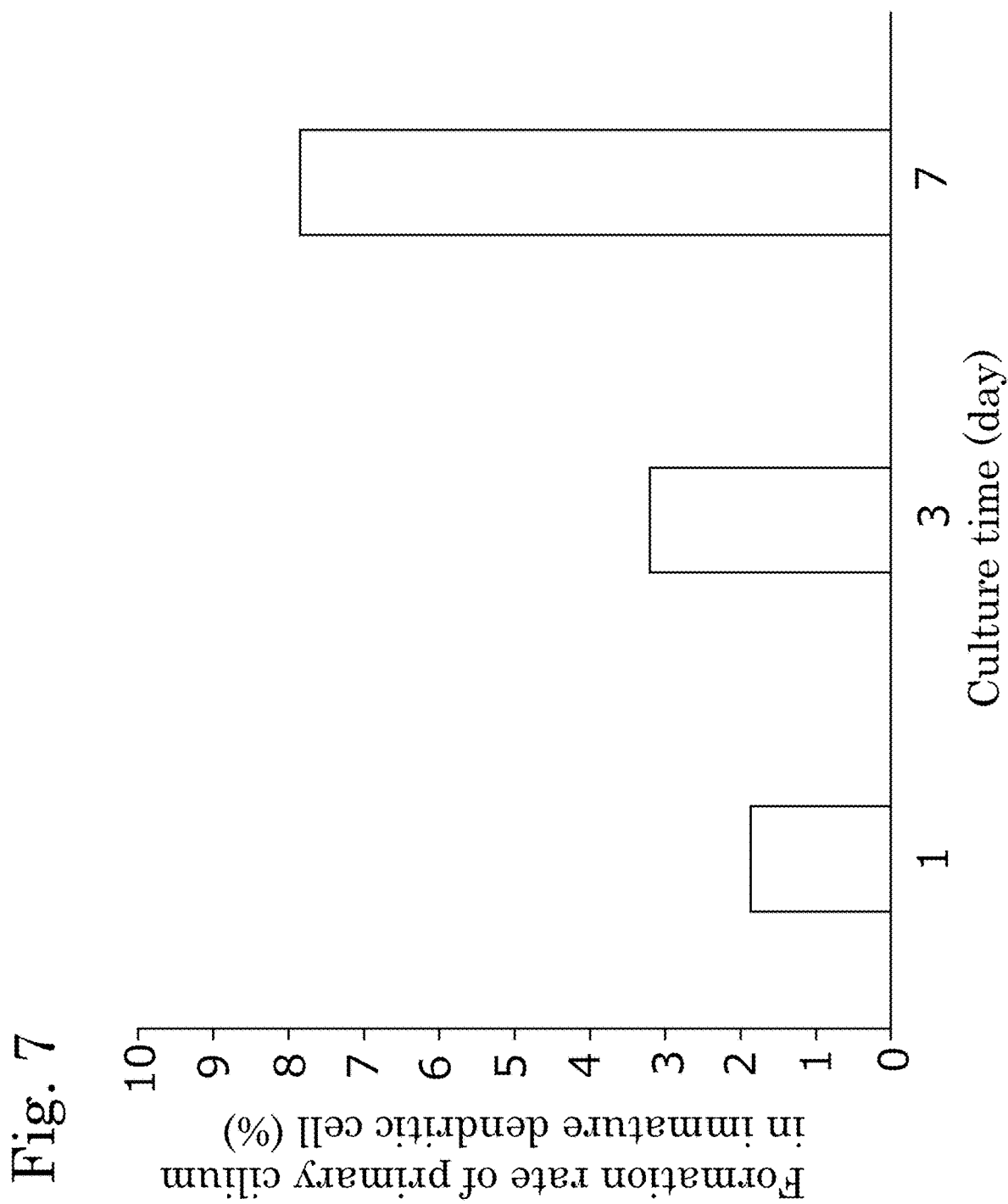
FIG. 7 is a graph showing results of examination of change in the formation rate of a primary cilium in an immature dendritic cell with the passage of time, examined in Example 4.

In Example 4, results of examination of change in the formation rate of a primary cilium in an immature dendritic cell with the passage of time are shown in FIG. 7.

From the results shown in FIGS. 6(A) to 6(C), it can be seen that the immature dendritic cell has a primary cilium. Additionally, from the results shown in FIG. 7, the formation rate of a primary cilium in an immature dendritic cell increases with the passage of culture time in an immature dendritic cell.

Example 5

Using 10 mL of peripheral blood collected from a healthy volunteer and 15 mL of human lymphocyte-separation medium (manufactured by GE Healthcare, trade name: Ficoll-Paque PLUS), peripheral blood mononuclear cells were separated from the peripheral blood, according to a density gradient centrifugation method. Immediately after separation, some of the peripheral blood mononuclear cells were fixed with 4 v/v % PFA-containing PBS solution. The fixed cells were blocked and permeabilized by incubating the fixed cell in a blocking/permeabilizing agent, to give a sample containing uncultured cells.

In addition, the rest of the separated peripheral blood mononuclear cells was cultured in a medium (RPMI 1640 medium containing 50 ng/mL IL-4, 50 ng/ml GM-CSF and 10 v/v % FBS) at 37° C. for 7 days, to give mature dendritic cells. In order to examine change in characteristics of the cells with the passage of time, each mature dendritic cell was collected after one day, three days and seven days passed from the initiation of culture. Immediately after collection, each of the collected mature dendritic cells was fixed with 4 v/v % PFA-containing PBS solution. The fixed cells were blocked and permeabilized by incubating the fixed cells in a blocking/permeabilizing agent, to give a sample containing mature dendritic cells after one day passed from the initiation of culture, a sample containing mature dendritic cells after three days passed from the initiation of culture, and a sample containing mature dendritic cells after seven days passed from the initiation of culture.

Each of the obtained samples was reacted with an anti-tubulin antibody (manufactured by Sigma-Aldrich, trade name: MONOCLONAL ANTI-ACETYLATED TUBULIN CLONE 6-11B-1, product number: T6793) and an anti-pericentrin antibody [manufactured by Bethyl Laboratories Inc., trade name: Pericentrin/Kendrin Antibody, product number: A301-348A-T] at a room temperature for 1 hour. Each of the reacted samples was washed with a washing solution A (0.1 w/w % polyoxyethylene sorbitan monolaurate (Tween-20)-containing PBS solution).

Each of the washed samples was stained by reacting the sample with a fluorescent dye-labeled anti-mouse IgG antibody [manufactured by Abcam, trade name: Goat Anti-Mouse IgG H&L (fluorescent dye: Alexa Fluor (registered trademark) 488, catalog number: ab150113)] and a fluorescent dye-labeled anti-rabbit IgG antibody [manufactured by Abcam, trade name: Goat Anti-Rabbit IgG H&L (fluorescent dye: Alexa Fluor (registered trademark) 594, catalog number: ab150080)] at a room temperature (25° C.) for 3 hours. Each of the stained samples was washed with the washing solution A.

Each of the washed sample was mounted in an antifade mountant [manufactured by Thermo Fisher Scientific K.K., trade name: ProLong (registered trademark) Gold antifade mountant, product number: P36934]. Using each of the obtained samples and a confocal microscope (manufactured by Olympus Corporation, product number: FV1200), a mature dendritic cell contained in each sample was observed by detecting a cell nucleus marker and a primary cilium marker contained in the samples.

Figure 8A:
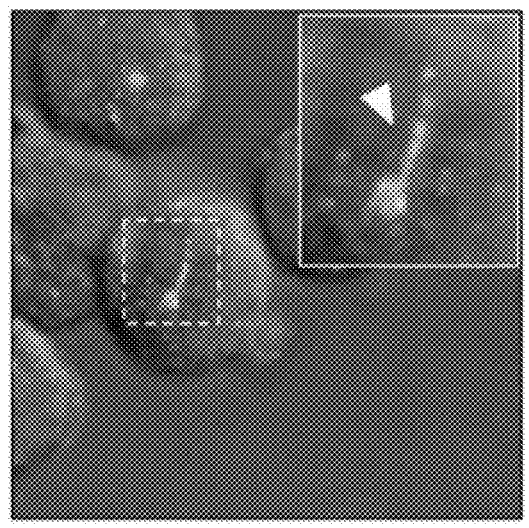
FIG. 8(A) is a photograph substituted for a drawing, showing observations of uncultured cells, examined in Example 5.
Figure 8B:
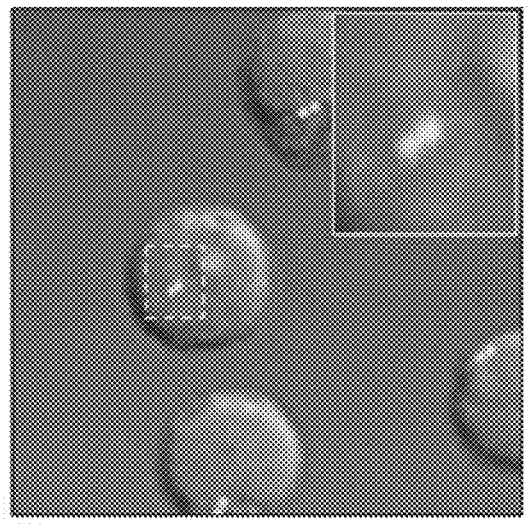
FIG. 8(B) is a photograph substituted for a drawing, showing observations of mature dendritic cells after one day passed from the initiation of the culture.
Figure 8C:
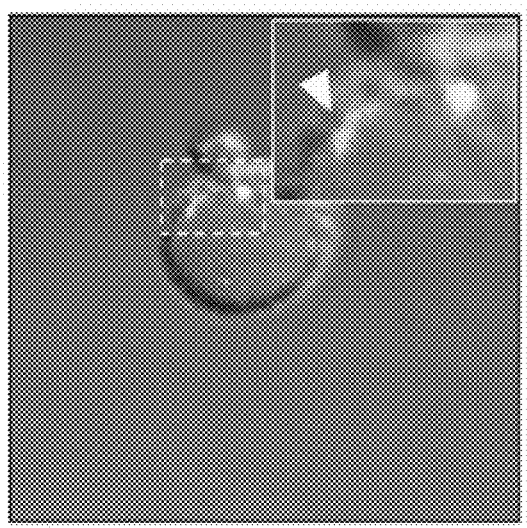
FIG. 8(C) is a photograph substituted for a drawing, showing observations of mature dendritic cells after three days passed from the initiation of the culture.
Figure 8D:
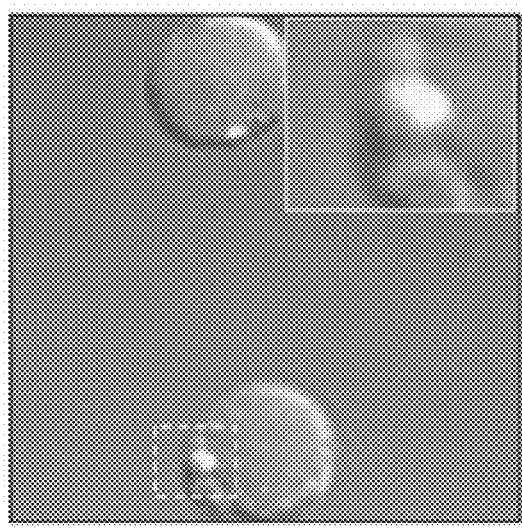
FIG. 8(D) is a photograph substituted for a drawing, showing observations of mature dendritic cells after seven days passed from the initiation of the culture.

In Example 5, observations of an uncultured cell are shown in FIG. 8(A); observations of a mature dendritic cell after one day passed from the initiation of culture are shown in FIG. 8(B); observations of a mature dendritic cell after three days passed from the initiation of culture are shown in FIG. 8(C); and observations of a mature dendritic cell after seven days passed from the initiation of culture are shown in FIG. 8(D). In the figures, a white arrow indicates a primary cilium marker, and the scale bar indicates 5 μm. In addition, a part surrounded by a white solid line is an enlarged view of a part surrounded by a broken line.

From the results shown in FIGS. 8(A) to 8(C), it can be seen that the uncultured cell and the mature dendritic cell after one day passed from the initiation of culture have a primary cilium.

Next, the number of total mature dendritic cells and the number of primary cilia in a mature dendritic cell were obtained by using the observations of the uncultured cells contained in the sample and the immature dendritic cells contained in the sample. Then, the formation rate of the primary cilium of a mature dendritic cell was calculated in accordance with the formula (Ib):

[Formation rate of primary cilium of mature dendritic cell]=[(Number of primary cilium in mature dendritic cell)/(Total number of mature dendritic cells)]×100         (Ib).

Figure 9:
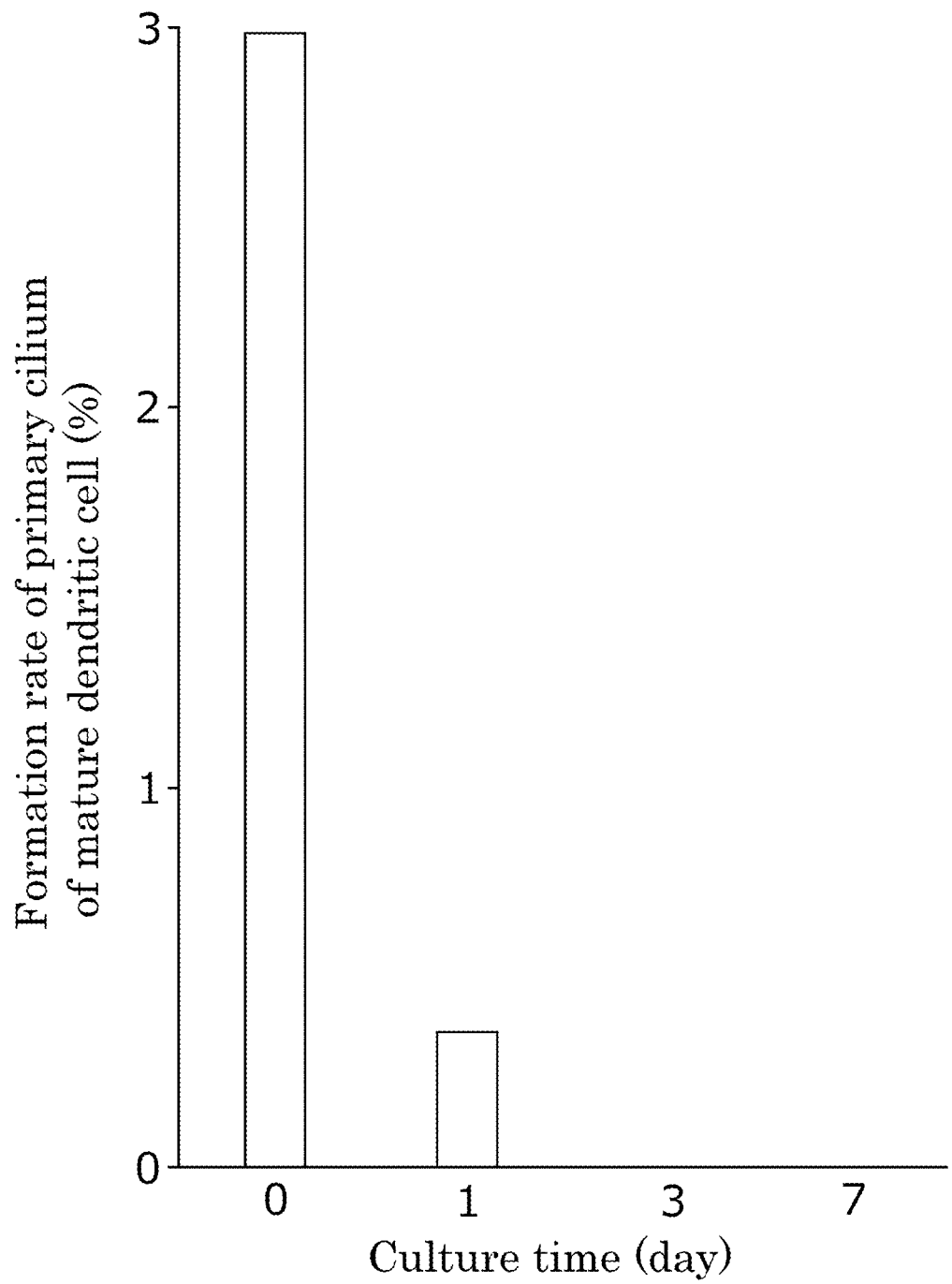
FIG. 9 is a graph showing results of examination of a change in the formation rate of a primary cilium of a mature dendritic cell with the passage of time, examined in Example 5.

Results of examination of change in the formation rate of a primary cilium in the mature dendritic cell with the passage of time are shown in FIG. 9. FIG. 9 is a graph showing the results of examination of change in the formation rate of a primary cilium of the mature dendritic cell with the passage of time in Example 5.

From the results shown in FIG. 9, it can be seen that the formation rate of a primary cilium in the mature dendritic cell decreases with the passage of culture time in the mature dendritic cell. From these results, it can be seen that the primary cilia decrease in association with maturation of a dendritic cell. Thus, it can be seen that the primary cilium of an immune cell is involved in proliferation of an immune cell.

Example 6

Using 10 mL of peripheral blood collected from an asthmatic patient and 15 mL of a human lymphocyte-separation medium (manufactured by GE Healthcare, trade name: Ficoll-Paque PLUS), peripheral blood mononuclear cells were separated from the peripheral blood, according to a density gradient centrifugation method. Some of the separated peripheral blood mononuclear cells were cultured in a steroid-containing medium (RPMI1640 medium containing 10 μM hydrocortisone or 10 μM dexamethasone, 0.1 v/v % DMSO and 10 v/v % FBS) or a control medium (RPMI1640 medium containing 0.1 v/v % DMSO and 10 v/v % FBS) in a culture vessel at 37° C. for 24 hours. The morphology and state of the obtained cell were observed by an inverted phase contrast microscope (manufactured by Leica Microsystems, trade name: DM IL LED).

In addition, the morphology and state of the obtained cells were observed in the same manner as those in the above, except that peripheral blood collected from a healthy volunteer was used in place of the peripheral blood collected from the asthmatic patient.

Figure 10A:
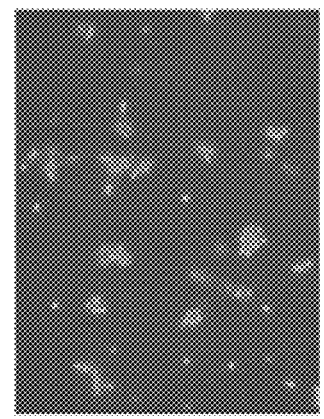
FIG. 10(A) is a photograph substituted for a drawing, showing observations of the morphology of nonadherent cells suspended in a control medium after culture in the control medium, examined in Example 6.
Figure 10B:
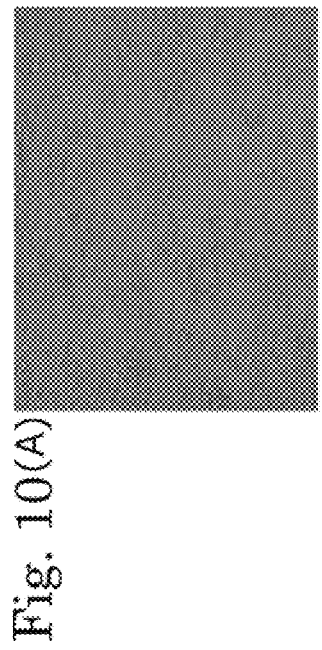
FIG. 10(B) is a photograph substituted for a drawing, showing observations of the morphology of cells adhered to a culture vessel after culture in a control medium.
Figure 10C:
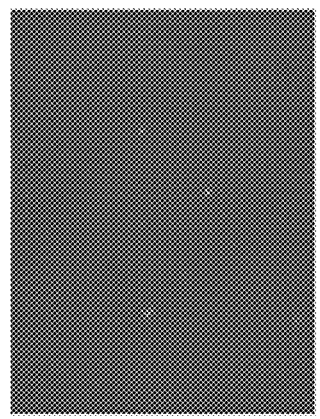
FIG. 10(C) is a photograph substituted for a drawing, showing observations of the morphology of nonadherent cells suspended in a hydrocortisone-containing medium after culture in the hydrocortisone-containing medium.
Figure 10D:
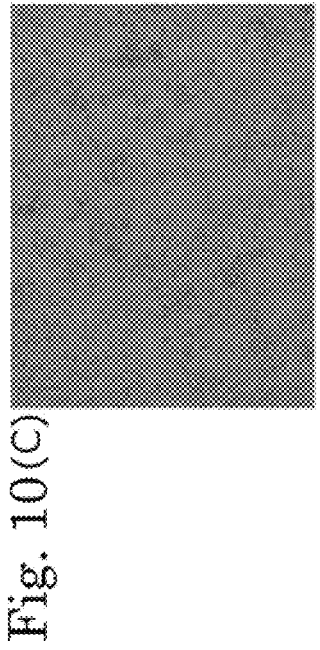
FIG. 10(D) is a photograph substituted for a drawing, showing observations of the morphology of cells adhered to a culture vessel after the culture in a hydrocortisone-containing medium.
Figure 10E:
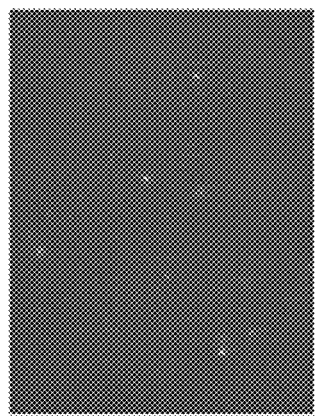
FIG. 10(E) is a photograph substituted for a drawing, showing observations of the morphology of nonadherent cells suspended in a dexamethasone-containing medium after culture in the dexamethasone-containing medium.
Figure 10F:
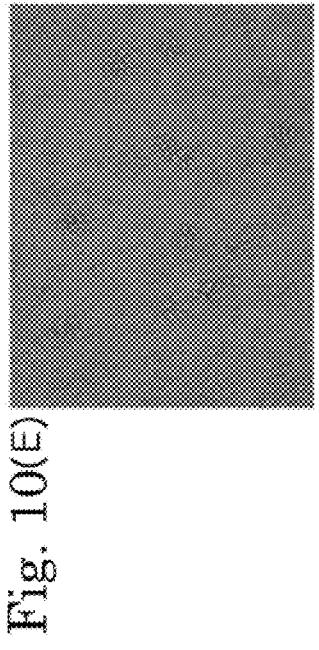
FIG. 10(F) is a photograph substituted for a drawing, showing observations of the morphology of cells adhered to a culture vessel after culture in a dexamethasone-containing medium.

In Example 6, observations of the morphology of nonadherent cells suspended in a control medium after culture in the control medium are shown in FIG. 10(A); observations of the morphology of cells adhering to a culture vessel after culture in a control medium are shown in FIG. 10(B); observations of the morphology of nonadherent cells suspended in a hydrocortisone-containing medium after culture in the medium are shown in FIG. 10(C); observations of the morphology of cells adhering to a culture vessel after culture in a hydrocortisone-containing medium are shown in FIG. 10(D); observations of the morphology of nonadherent cells suspended in a dexamethasone-containing medium after culture in the medium are shown in FIG. 10(E); and observations of the morphology of cells adhering to a culture vessel after culture in a dexamethasone-containing medium are shown in FIG. 10(F). In the figures, the scale bar indicates 100 μm.

From the results shown in FIGS. 10(A) to 10(F), it can be seen that a cell group obtained from peripheral blood collected from an asthmatic patient contains an adhesive cell having a morphology different from a nonadherent cell (see FIG. 10(A), FIG. 10(C) and FIG. 10(E)), and high adhesiveness to a culture vessel (see FIG. 10(B), FIG. 10(D) and FIG. 10(F)). Additionally, presence of a cell having the same adhesiveness to a culture vessel as the adhesive cell and having the same morphology as the adhesive cell was not confirmed in a cell group obtained from peripheral blood collected from a healthy volunteer. Accordingly, it can be seen that the adhesive cell is a cell characteristic in asthma.

In addition, from the results shown in FIGS. 10(A) to 10(F), it can be seen that, when an adhesive cell is cultured with hydrocortisone or dexamethasone, which are steroids, the adhesive cell disappears. On the other hand, it can be seen that, when the adhesive cell is cultured in a control medium containing no steroid, the adhesive cell is not decreased.

Example 7

Using 10 mL of peripheral blood collected from an asthmatic patient and 15 mL of a human lymphocyte-separation medium (manufactured by GE Healthcare, trade name: Ficoll-Paque PLUS), peripheral blood mononuclear cells were separated from the peripheral blood, according to a density gradient centrifugation method. Some of the separated peripheral blood mononuclear cells were fixed with 4 v/v % PFA-containing PBS solution. The fixed cells were blocked and permeabilized by incubating the cells in a blocking/permeabilizing agent, to give a sample containing uncultured cells.

Some of the separated peripheral blood mononuclear cells were cultured in a steroid-containing medium (RPMI1640 medium containing 10 μM hydrocortisone or 10 μM dexamethasone, 0.1 v/v % DMSO and 10 v/v % FBS) at 37° C. for 24 hours. Then, nonadherent cells suspended in each medium were collected. Immediately after collection, each of the collected cells was fixed with 4 v/v % PFA-containing PBS solution. The fixed cells were blocked and permeabilized by incubating the fixed cells in a blocking/permeabilizing agent, to give a sample containing cells after one day passed from the initiation of culture, a sample containing cells after three days passed from the initiation of culture, and a sample containing cells after seven days passed from the initiation of culture.

Each of the obtained samples was reacted with an anti-tubulin antibody (manufactured by Sigma-Aldrich, trade name: MONOCLONAL ANTI-ACETYLATED TUBULIN CLONE 6-11B-1, product number: T6793) and an anti-pericentrin antibody (manufactured by Bethyl Laboratories Inc., trade name: Pericentrin/Kendrin Antibody A301-348A-T) at a room temperature for 1 hour. Each of the reacted samples was washed with a washing solution A (0.1 w/w % polyoxyethylene sorbitan monolaurate (Tween-20)-containing solution).

Each of the washed samples was stained by reacting the sample with a fluorescent dye-labeled anti-mouse IgG antibody [manufactured by Abcam, trade name: Goat Anti-Mouse IgG H&L (fluorescent dye: Alexa Fluor (registered trademark) 488), catalog number: ab150113] and a fluorescent dye-labeled anti-rabbit IgG antibody [manufactured by Abcam, trade name: Goat Anti-Rabbit IgG H&L (fluorescent dye: Alexa Fluor (registered trademark) 594, catalog number: ab150080)] at a room temperature (25° C.) for 1 hour. Each of the stained samples was washed with the washing solution A.

Each of the washed sample was mounted in an antifade mountant [manufactured by Thermo Fisher Scientific K.K., trade name: ProLong (registered trademark) Gold antifade mountant, product number: P36934]. Using each of the obtained samples and a confocal microscope (manufactured by Olympus Corporation, product number: FV1200), a cell contained in each sample was observed by detecting a cell nucleus marker and a primary cilium marker contained in the sample.

Next, the total number of immune cells and the number of primary cilia in an immune cell were obtained by using observations of cells contained in each sample. Then, the formation rate of a primary cilium in an immune cell was calculated in accordance with the formula (Ic):

[Formation rate of primary cilium in immune cell]= [(Number of primary cilia in immune cell)/(Total number of immune cells)]×100  (Ic).

In addition, the formation rate of primary cilium in the immune cell was calculated in the same manner as those in the above, except that a control medium (RPMI1640 medium containing 0.1 v/v % DMSO and 10 v/v % FBS) was used in place of the steroid-containing medium, and that each sample was obtained by separating the cells after culture in the control medium into nonadherent cells and adhesive cells, collecting separately each of the nonadherent cells and adhesive cells, fixing each of the collected nonadherent cells and the collected adhesive cells immediately after the collection with 4 v/v % PFA-containing PBS solution, and incubating each of the fixed cells in a blocking/permeabilizing agent to block and permeabilize the fixed cells.

Figure 11:
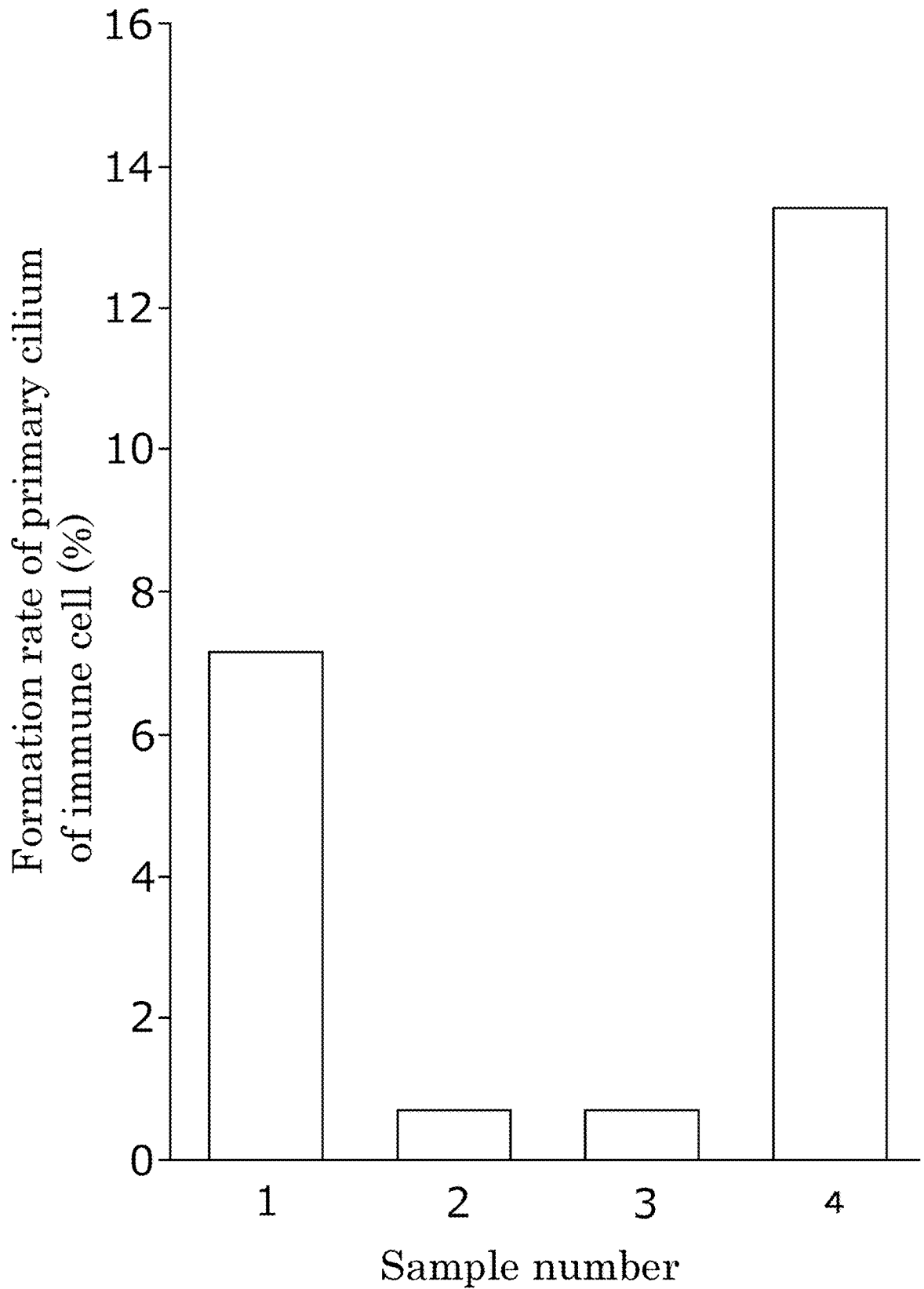
FIG. 11 is a graph showing results of examination of the relationship between the kind of the sample and the formation rate of a primary cilium of an immune cell, examined in Example 7.

Results of examination of the relationship between the kind of the sample and the formation rate of a primary cilium of an immune cell are shown in FIG. 11. FIG. 11 is a graph showing results of examination of the relationship between the kind of the sample and the formation rate of a primary cilium of the immune cell in Example 7. In the figures, a sample number 1 denotes the formation rate of a primary cilium of the immune cell in the nonadherent cell after culture in a control medium; a sample number 2 denotes the formation rate of a primary cilium of the immune cell in the nonadherent cell after culture in a hydrocortisone-containing medium; a sample number 3 denotes the formation rate of a primary cilium of the immune cell in the nonadherent cell after culture in a dexamethasone-containing medium; and a sample number 4 denotes the formation rate of a primary cilium of the immune cell in the adhesive cell after culture in a control medium.

From the results shown in FIG. 11, it can be seen that the formation rate of a primary cilium of the immune cell in the nonadherent cell after culture in a hydrocortisone-containing medium and the formation rate of a primary cilium of the immune cell in the nonadherent cell after culture in a dexamethasone-containing medium are significantly lower than the formation rate of a primary cilium of the immune cell in the nonadherent cell after culture in a control medium.

In addition, it can be seen that an adhesive cell after culture in a control medium has high formation rate of a primary cilium of an immune cell.

A cell group obtained from peripheral blood obtained from an asthmatic patient before administration of a steroid, which is an immune-related disease inhibitor was compared with a cell group obtained from peripheral blood of a patient administered with a steroid and whose symptom has been remitted. As a result, although the cell group obtained from peripheral blood before administration of the steroid contained a large number of adhesive cells each having a primary cilium. However, adhesive cells each including an adhesive cell having a primary cilium were not confirmed in the cell group obtained from peripheral blood after administration of the steroid. From these results, it can be seen that the number of primary cilia in an immune cell correlates with an immune-related disease. In addition, it can be seen that the primary cilium in an immune cell is involved in an immune-related disease.

From the above results, it can be seen that as an index of an suppression effect on the immune-related disease, change in the number of primary cilia of the immune cells in the subject between before and after the treatment or between before and after the administration of the immune-related disease inhibitor can be used, which is obtained by measuring the number of primary cilia of the immune cells in the subject specimen before and after the treatment or before and after the administration of the immune-related disease inhibitor, which was collected from the subject, and comparing the numbers of primary cilia of the immune cell in the subject specimen between before and after the treatment or between before and after the administration of the immune-related disease inhibitor with each other.

Example 8

The number A of primary cilia of keratinocytes in a cell group containing keratinocytes each having a primary cilium is measured. A test sample is obtained by dissolving a low molecular weight compound, a polymer compound, a plant extract, and the like in a solvent such as PBS. Next, the cell group is contacted with the test sample such as a low molecular weight compound, a polymer compound, a plant extract, and the like. After the contact, the number B of primary cilia of keratinocytes in a cell group contacted with the test sample is measured. A difference between the number A of primary cilia of keratinocytes and the number B of primary cilia of keratinocytes is obtained. When the number B of primary cilia of keratinocytes is significantly larger than the number A of primary cilia of keratinocytes, it can be evaluated that the test sample has an immune function-promoting action. When the number B of primary cilia of keratinocytes is significantly smaller than the number A of primary cilia in keratinocytes, it can be evaluated that the test sample has an immune function-suppressing action. Additionally, even when other immune-related cells are used in place of the keratinocytes in the above, the immune function-promoting action or the immune function-suppressing action of the test sample can be evaluated in the same manner as in the case where the keratinocytes are used.

Example 9

Using the number of Langerhans cells each having a primary cilium as an observation item, cells contained in an observation sample derived from a human healthy skin tissue (normal tissue) obtained in the same manner as in Example 1 and an observation sample derived from an atopic dermatitis lesion tissue obtained in the same manner as in Example 2 were observed, to count the number of Langerhans cells each having a primary cilium. Using the number of cells of the observed cell population and the number of Langerhans cells each having a primary cilium, the content of Langerhans cells each having a primary cilium in a cell population was obtained in accordance with the formula (II):

[Content of Langerhans cell having primary cilium in cell population]=[(Number of Langerhans cells having primary cilium)/(Number of cells in cell population)]×100  (II).

Figure 12:
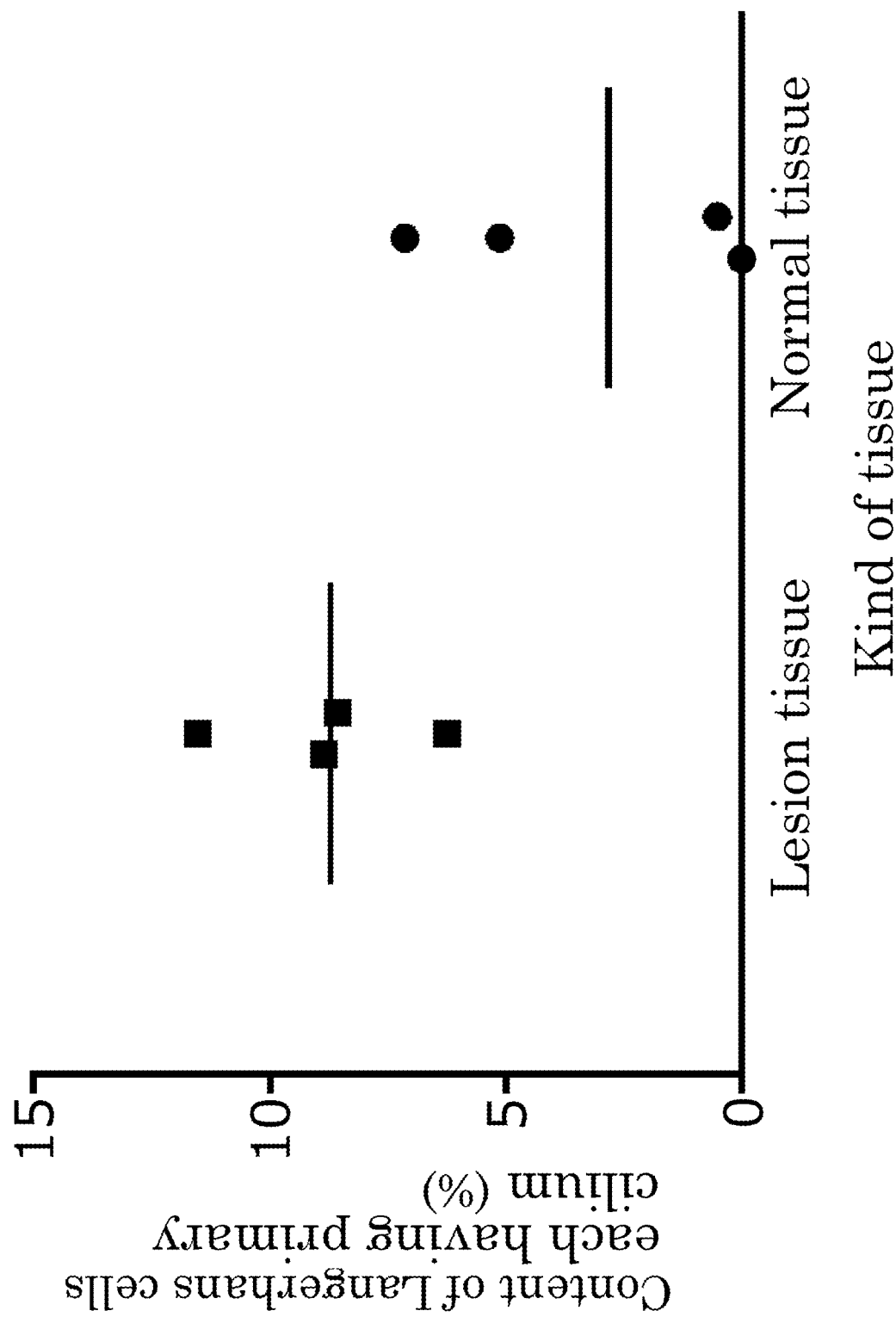
FIG. 12 is a graph showing results of examination of the relationship between the kind of the tissue and the content of Langerhans cells each having a primary cilium in a cell population, examined in Example 9.

Results of examination of the relationship between the kind of the tissue and the content of Langerhans cells each having a primary cilium in a cell population are shown in FIG. 12. FIG. 12 is a graph showing results of examination of the relationship between the kind of the tissue and the content of Langerhans cells each having a primary cilium in a cell population in Example 9. In the figures, "Content of Langerhans cells each having a primary cilium" means the content of Langerhans cells each having a primary cilium in a cell population.

From the results shown in FIG. 12, it can be seen that the content of Langerhans cells each having a primary cilium in a cell population in the atopic dermatitis lesion tissue is higher than that in the normal tissue.

In addition, using the number of keratinocytes each having a primary cilium as an observation item, cells contained in each of an observation sample derived from a human healthy skin tissue (normal tissue) obtained in the same manner as in Example 1 and an observation sample derived from an atopic dermatitis lesion tissue obtained in the same manner as in Example 2 are observed, to count the number of keratinocytes each having a primary cilium. Using the number of cells of the observed cell population and the number of keratinocytes each having a primary cilium, the content of keratinocytes each having a primary cilium in a cell population was obtained in accordance with the formula (III):

[Content of keratinocytes each having primary cilium in cell population]=[(Number of keratinocytes each having primary cilium)/(Number of cells in cell population)]×100  (III).

Figure 13:
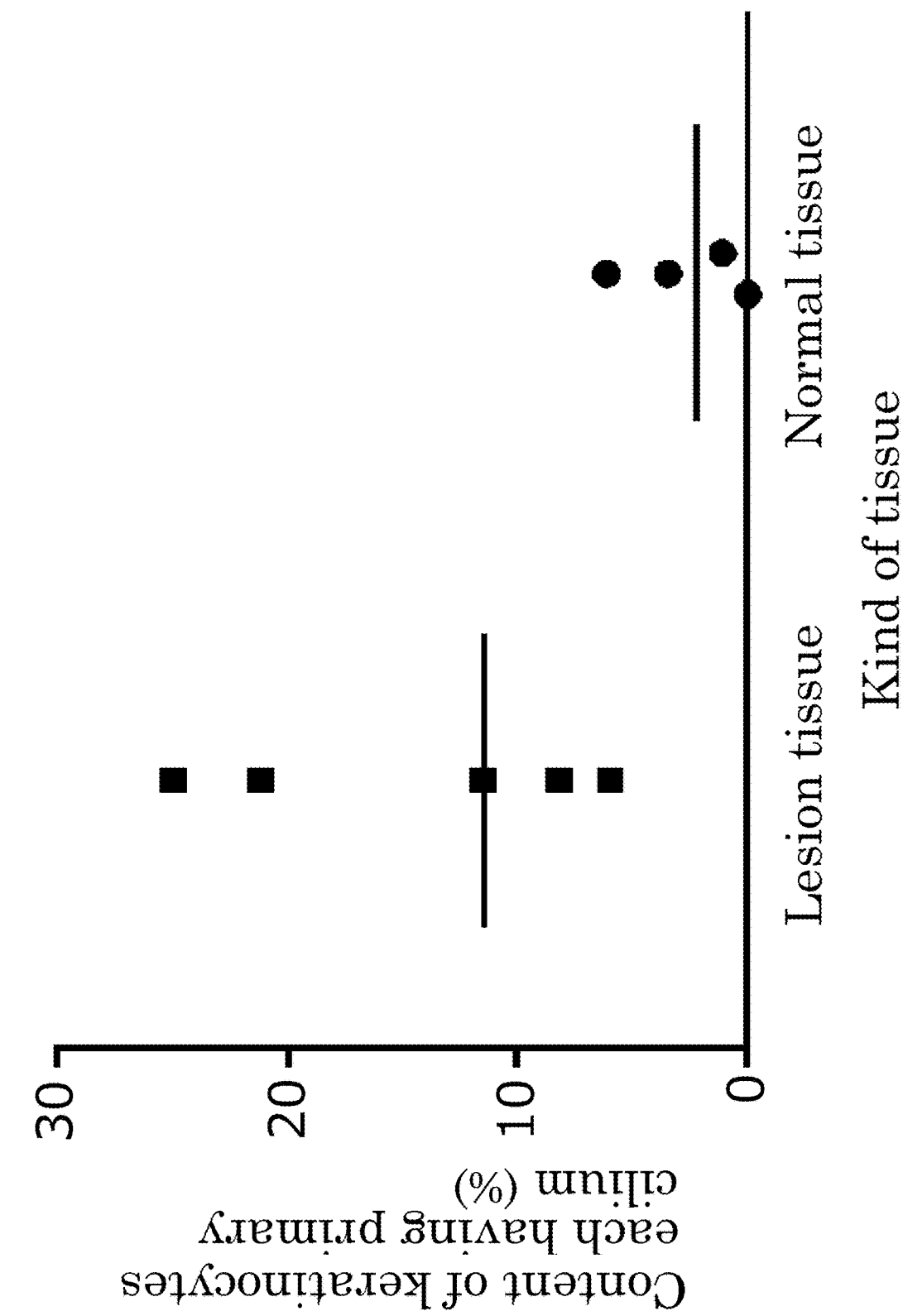
FIG. 13 is a graph showing results of examination of the relationship between the kind of the tissue and the content of keratinocytes each having a primary cilium in a cell population, examined, examined in Example 9.

Result of examining the relationship between the kind of the tissue and the content of keratinocytes each having a primary cilium in a cell population are shown in FIG. 13. FIG. 13 is a graph showing results of examination of the relationship between the kind of the tissue and the content of keratinocytes each having a primary cilium in the cell population in example 9. In the figures, "content of keratinocytes each having a primary cilium" means the content of keratinocytes each having a primary cilium in a cell population.

From the results shown in FIG. 13, it can be seen that the content of keratinocytes each having a primary cilium in the cell population in the atopic dermatitis lesion tissue is higher than that in the normal tissue.

From these results, it can be seen that the increase in Langerhans cells each having a primary cilium and keratinocytes each having a primary cilium is associated with atopic dermatitis.

As explained above, since the primary cilium of the immune-related cell correlates with the immune-related disease, it can be seen that detection of an index of the immune-related disease, assistance in diagnosis of the presence or absence of affection with the immune-related disease, assistance in diagnosis of prognosis of the immune-related disease, evaluation of the suppression effect of the treatment of the immune-related disease or the immune-related disease inhibitor on the immune-related disease, and evaluation of whether or not the test sample is a substance possessing an immune function-controlling action can be performed by observing the primary cilium in the immune-related cell. In addition, since a primary cilium of an immune-related cell is involved in proliferation of an immune-related cell and an immune-related disease, it can be seen that the immune function can be controlled by regulating formation of a primary cilium of an immune-related cell. Accordingly, the present invention is expected to be used for examination of an immune-related disease, assistance in diagnosis of the presence or absence of affection with an immune-related disease, assistance in diagnosis of prognosis of an immune-related disease, development of a therapeutic agent for an immune-related disease, development of a quasi-drug or a cosmetic component for suppressing an immune-related disease, and the like.

REFERENCE SIGNS LIST 1 epidermis
2 dermis

The invention claimed is:
1. A method for detecting an index of an immune-related disease in a subject specimen collected from a subject, comprising the steps of:

observing primary cilia of immune-related cells in the subject specimen and primary cilia of immune-related cells in a normal specimen, counting a number of immune-related cells having the primary cilia or measuring a length of the primary cilia, comparing the number of immune-related cells having the primary cilia or the length of the primary cilia of the immune-related cells in the subject specimen with the number of immune-related cells having the primary cilia or the length of the primary cilia of the immune-related cells in the normal specimen, detecting a difference in the number of immune-related cells having the primary cilia or the length of the primary cilia between the primary cilia of the immune-related cells in the subject specimen and the primary cilia of the immune-related cells in the normal specimen, and using the difference as an index of the immune-related disease, wherein the immune-related disease is atopic dermatitis or asthma, and the immune-related cells are Langerhans cells, keratinocytes, or peripheral blood mononuclear cells, and wherein the index is a formation rate of primary cilia of immune-related cells in the subject specimen being either higher or lower than a formation rate of primary cilia of immune-related cells in the normal specimen.

2. A method for assisting diagnosis of an immune-related disease in a subject, comprising the steps of:

observing primary cilia of immune-related cells in a subject specimen collected from the subject and primary cilia of immune-related cells in a normal specimen to be compared, counting a number of immune-related cells having the primary cilia or measuring a length of the primary cilia, comparing the number of immune-related cells having the primary cilia or the length of the primary cilia of the immune-related cells in the subject specimen with the number of immune-related cells having the primary cilia or the length of the primary cilia of the immune-related cells in the normal specimen to be compared, and obtaining a comparison result indicating that the number of immune-related cells each having the primary cilia in the subject specimen is larger than the number of immune-related cells each having primary cilia in the normal specimen to be compared, a comparison result indicating that the formation rate of the primary cilia of the immune-related cells in the subject specimen is higher than the formation rate of the primary cilia of the immune-related cells in the normal specimen to be compared, or a comparison result indicating that the length of the primary cilia of the immune-related cells in the subject specimen is longer than the length of the primary cilia of the immune-related cells in the normal specimen to be compared, and providing the comparison result to a doctor for a diagnosis by the doctor of the presence or absence of infection with the immune-related disease in the subject or information for assisting diagnosis or prognosis of the immune-related disease in the subject, on the basis of the resulting comparison result, wherein the immune-related disease is atopic dermatitis or asthma, and the immune-related cells are Langerhans cells, keratinocytes, or peripheral blood mononuclear cells, and wherein the index is a formation rate of primary cilia of immune-related cells in the subject specimen being either higher or lower than a formation rate of primary cilia of immune-related cells in the normal specimen.

3. The method for detecting an index of an immune-related disease in a subject of claim 1, wherein the immune-related disease is atopic dermatitis.

4. The method for detecting an index of an immune-related disease in a subject of claim 1, wherein the immune-related disease is asthma.

5. The method for assisting diagnosis of an immune-related disease in a subject of claim 2, wherein the immune-related disease is atopic dermatitis.

6. The method for assisting diagnosis of an immune-related disease in a subject of claim 2, wherein the immune-related disease is asthma.

7. The method for detecting an index of an immune-related disease in a subject of claim 1, wherein the immune-related cells are Langerhans cells.

8. The method for detecting an index of an immune-related disease in a subject of claim 1, wherein the immune-related cells are keratinocytes.

9. The method for detecting an index of an immune-related disease in a subject of claim 1, wherein the immune-related cells are peripheral blood mononuclear cells.

* * * * *